United States Patent
Zheng et al.

(10) Patent No.: US 8,277,791 B2
(45) Date of Patent: Oct. 2, 2012

(54) COSMETIC COMPOSITIONS HAVING IMPROVED TRANSFER RESISTANCE

(75) Inventors: Tao Zheng, Nanuet, NY (US); Leona G. Fleissman, Ridgewood, NJ (US); Maha Raouf, Franklin Lakes, NJ (US); Sonal Patel, Jersey City, NJ (US)

(73) Assignee: Avon Products, Inc., New York, NY (US)

( * ) Notice: Subject to any disclaimer, the term of this patent is extended or adjusted under 35 U.S.C. 154(b) by 562 days.

(21) Appl. No.: 11/810,559

(22) Filed: Jun. 6, 2007

(65) Prior Publication Data

US 2008/0305068 A1    Dec. 11, 2008

(51) Int. Cl.
*A61K 31/74* (2006.01)
*A61K 8/02* (2006.01)

(52) U.S. Cl. .................... 424/78.03; 424/401

(58) Field of Classification Search .................. None
See application file for complete search history.

(56) References Cited

U.S. PATENT DOCUMENTS

| | | | |
|---|---|---|---|
| 4,035,313 A * | 7/1977 | Falkenstein et al. | 521/160 |
| 4,578,266 A | 3/1986 | Tietjen et al. | |
| 4,699,780 A | 10/1987 | Jennings et al. | |
| 5,318,775 A | 6/1994 | Shore et al. | |
| 5,643,581 A | 7/1997 | Mougin et al. | |
| 6,120,753 A | 9/2000 | Vinski et al. | |
| 6,166,093 A | 12/2000 | Mougin et al. | |
| 6,406,683 B1 * | 6/2002 | Drechsler et al. | 424/64 |
| 6,780,402 B1 | 8/2004 | Agostini et al. | |
| 2005/0129641 A1 * | 6/2005 | Arnaud et al. | 424/63 |
| 2005/0238611 A1 * | 10/2005 | Rando et al. | 424/70.122 |
| 2006/0018856 A1 * | 1/2006 | Bosman et al. | 424/70.12 |

* cited by examiner

*Primary Examiner* — David J Blanchard
*Assistant Examiner* — Melissa Javier
(74) *Attorney, Agent, or Firm* — Joan M. McGillycuddy; Charles J. Zeller; David M. Joyal

(57) ABSTRACT

Cosmetic compositions and methods with improved transfer resistance and long wear properties are disclosed. The cosmetic compositions contain a synergistic combination of at least one silicone polyurethane polymer and at least one elastomer.

22 Claims, 7 Drawing Sheets

COSMETIC COMPOSITIONS HAVING IMPROVED TRANSFER RESISTANCE

FIELD OF INVENTION

The present invention relates generally to long wearing, transfer resistance cosmetics such as lipstick, mascara and the like.

BACKGROUND OF THE INVENTION

Many cosmetics and personal care products employ various film forming agents to aid in spreading and adhering a formulation to a surface such as skin. The class of polymers known as organosiloxanes, including polydimethylsiloxane (PDMS or Dimethicone), have recently received considerable attention as film-formers in cosmetic products due to their excellent spreading properties and biological inertness. Examples of cosmetic formulations including organosiloxane film formers include, for example, U.S. Pat. No. 6,780,402 (L'Oreal), U.S. Pat. No. 5,318,775 (Mary Kay Cosmetics), U.S. Pat. No. 4,699,780 (Estee Lauder); and U.S. Pat. No. 4,578,266 (Revlon), the disclosures of which are hereby incorporated by reference. Recent advances have included the use of polyorganosiloxane polyurethane polymers.

For example, U.S. Patent Publication No. 2005/0238611 describes cosmetic compositions comprising a particular silicone polyurethane which is the reaction product of a silicone pre-polymer with a diisocyanate. The silicone pre-polymer is an alkoxylated, bis-hydroxyalkyl group terminated polydialkylsiloxane, in which the reactive —OH group is attached to a carbon atom. It is stated that the use of the particular silicone-containing polyurethane provides improved film-forming properties and imparts transfer-resistance.

U.S. Pat. No. 6,166,093 describes polyurethane block condensation products comprising a polysiloxane graft and their use as film-formers in treating keratinous materials.

U.S. Pat. No. 5,643,581 describes cosmetic compositions comprising a pseudolatex based on a multiblock polycondensate which contains a polysiloxane block and a polyurethane and/or polyurea block wherein the polyurethane and/or polyurea block further comprises anionic or cationic groups.

U.S. Pat. No. 6,120,753 describes skin cleansing compositions, said to have moisturizing properties, which comprise a urethane siloxane copolymer.

Despite the advances in film forming methods and compositions, there remains a need in the art for improved transfer resistance and long wear properties for cosmetic compositions for the skin and hair.

It is therefore an object of the invention to provide compositions and methods for improved transfer resistance and long wear properties for cosmetic compositions for the skin and hair.

SUMMARY OF INVENTION

In accordance with the foregoing objectives and others, the present invention provides cosmetic compositions which are resistant to transfer, durable, and comfortable to wear. More particularly, the invention relates to cosmetic compositions containing at least one silicone polyurethane polymer in combination with at least one elastomer, typically in a suitable cosmetic vehicle. Compositions according to the invention may be applied to the skin, including the lips, or hair, including eyelashes, eyebrows, hairs of the scalp and the like. The composition impart a durable film resistant to transfer upon contact with objects such as clothing, napkins, etc.

In one aspect of the invention, long-wearing, transfer resistant cosmetic compositions for application to the skin or hair are provided. Such compositions provide a durable deposit upon the skin or hair that resists degradation over time. The cosmetic compositions will typically comprise: (i) at least one silicone polyurethane polymer; and (ii) at least one elastomer; wherein the weight ratio of silicone polyurethane polymer to elastomer is from about 50:1 to about 1:50, typically, from about 10:1 to about 1:10, and preferably from about 5:1 to 1:5. The at least one elastomer will preferably be selected from the group consisting of silicone gums, polyisobutylene, natural rubbers, and block-copolymer rubbers.

In another aspect of the invention, long-wearing, transfer resistant cosmetic compositions are provided comprising: (i) at least one silicone polyurethane polymer; and (ii) at least one elastomer selected from the group consisting of silicone gums, polyisobutylene, natural rubbers, and block-copolymer rubbers; wherein the weight ratio of silicone polyurethane polymer to elastomer is from about 50:1 to about 1:50; wherein the composition provides a improvement in at least one characteristic selected from the groups consisting of water transfer resistance, oil transfer resistance, flexibility, storage modulus (G'), loss modulus (G''), and/or loss tangent ($\tan(\delta)$). Preferably, the improvement in at least one characteristic will include an improvement in water transfer resistance and/or oil transfer resistance, more preferably a synergistic improvement in water transfer resistance and/or oil transfer resistance.

In a further aspect of the invention, the cosmetic compositions will comprise:

(1) at least one silicone polyurethane polymer which is the reaction product of:

(a) an hydroxyl functionalized polydimethylsiloxane of the form:

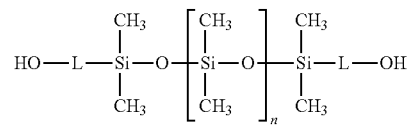

where L is a bond or a linker group selected from divalent $C_{1-10}$ hydrocarbons; and n is an integer from 0 to 5,000 and, (b) a diisocyante of the form O=C=N—R$^1$—N=C=O, where R$^1$ is a divalent moiety selected from the groups consisting of:

(i) a group of the form:

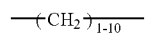

(ii) a group of the form:

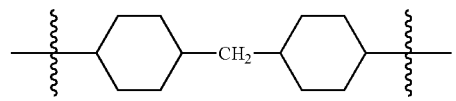

(iii) a group of the form:

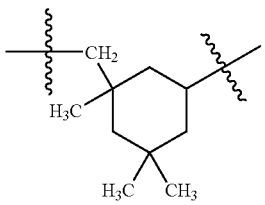

(iv) a group of the form:

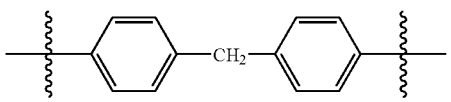

and;

(v) a group of the form:

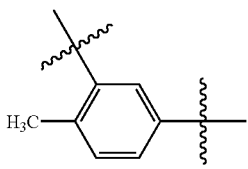

and combinations thereof; and (2) at least one elastomer selected from the group consisting of silicone gums, polyisobutylene, natural rubbers, and block-copolymer rubbers; and (3) a cosmetically acceptable vehicle, wherein the silicone polyurethane polymer and elastomer are present in a weight ratio from about 50:1 to about 1:50; and wherein said composition provides a synergistic improvement in water transfer resistance.

In another aspect of the invention, a method is provided for forming transfer resistant and/or long-wearing film on skin or keratin fibers comprising applying a composition according to the invention to skin or keratin fibers, wherein the composition comprises a synergistic combination of a silicone polyurethane polymer and an elastomer. The resultant film is expected to have improved durability and/or transfer resistance on skin or keratin fibers for a long-wear period such as from about 1 to about 24 hours, as compared to an otherwise identical composition which does not comprise the synergistic combination.

In one variant according to this aspect of the invention, a method for imparting a transfer resistant and/or long wearing film to skin or keratin fibers is provided comprising applying to the skin or keratin fibers a cosmetic or personal care composition comprising, in a suitable vehicle, a synergistic combination of:

a) at least one silicone polyurethane polymer; and b) at least one polyorganosiloxane gum having a viscosity of from about 500,000 cst to about 5,000,000 cst at 25 degrees Celsius; wherein said synergistic combination comprises a weight ratio from about 50:1 to about 1:50 of the at least one silicone polyurethane polymer to the at least one polyorganosiloxane gum.

In yet another aspect of the invention, a method for imparting a transfer resistant and/or long wearing film to the skin or keratin fibers is provided comprising applying to skin or keratin fibers a cosmetic or personal care composition comprising, in a suitable vehicle, a synergistic combination of:

a) at least one silicone polyurethane polymer; and b) at least one polyisobutylene elastomer; wherein said synergistic combination comprises a weight ratio from about 50:1 to about 1:50 of the at least one silicone polyurethane polymer to the at least one polyorganosiloxane gum.

These and other aspects of the present invention will become apparent to those skilled in the art after a reading of the following detailed description of the invention, including the illustrative embodiments and examples.

BRIEF DESCRIPTION OF THE DRAWINGS

FIG. 1 illustrates the water transfer resistance of lip gloss formulations comprising silicone polyurethane in the absence of an elastomer (♦) as a function of the amount of silicone polyurethane (by weight %) compared to the water transfer resistance of lip gloss formulations comprising varying concentrations of silicone polyurethane in combination with 6 weight % silicone gum elastomer (■), and a lip gloss formulation comprising silicone polyurethane in combination with 12% by weight silicone gum (▲).

DETAILED DESCRIPTION

Figure 1:
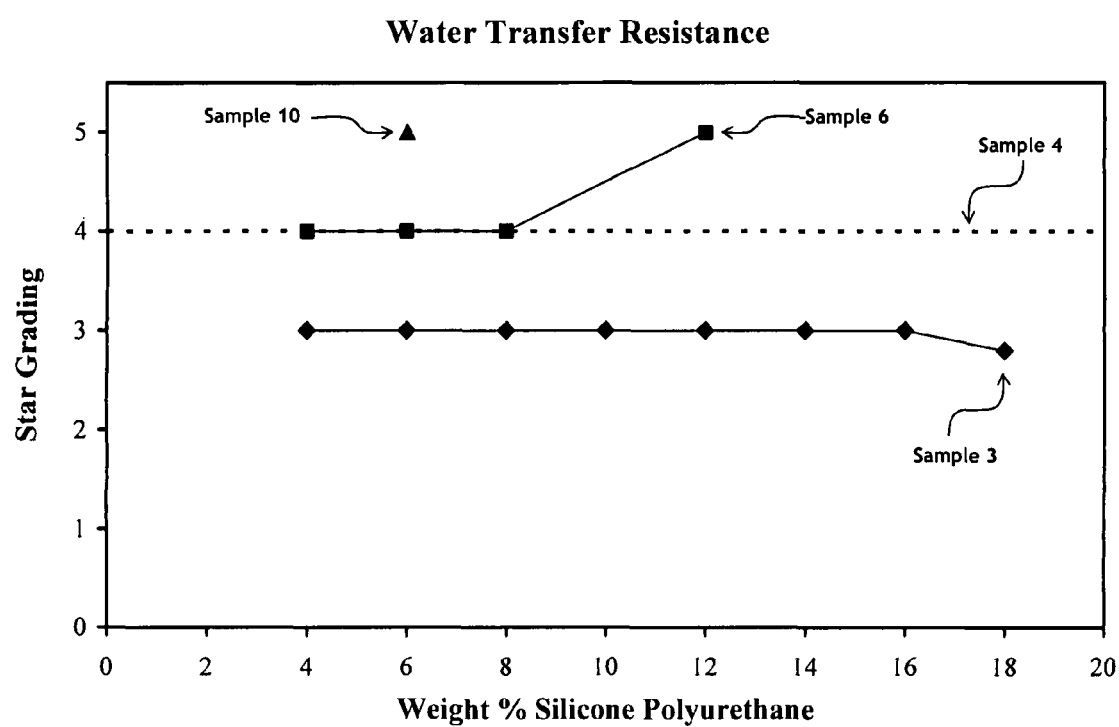
FIG. 1 shows the water transfer resistance of exemplary lip gloss formulations as a function of the percentage by weight of silicone polyurethane polymer.

The present invention is founded on the discovery that combinations of certain silicone polyurethane polymers and elastomers provide a synergistic result in their long wearing, transfer resistant properties for cosmetic compositions when applied to biological surfaces. As used herein, the term "biological surface" is meant to include any surface to which cosmetic and personal care products are applied, including without limitation, skin (including lips), hair (including eyelashes, eyebrows or hairs of the scalp), and nails.

The composition generally comprise a silicone polyurethane polymers in combination with a elastomer. The combination of these components provides a synergistic improvement in transfer resistance of the cosmetic. By "synergistic improvement" is meant that the combination of silicone polyurethane polymer and elastomer improves one or more characteristics of the cosmetic as compared to otherwise identical compositions lacking either the silicone polyurethane polymer or the elastomer. The improvement may manifest in a variety characteristics, but typically will relate to the viscoelastic properties of the applied film. The viscoelasticity of the cosmetic film provides substantivity to the skin and thus will contribute to long-wear, flexibility, and transfer resistance to both oily and watery, substrates. The viscoelastic properties may be quantified on the basis of storage modulus G', loss modulus G", and loss tangent tan (δ) which is the ratio of G"/G'. Thus, the synergistic improvement may be an improvement in one or more characteristics selected from length of wear, flexibility, water transfer resistance, oil transfer resistance, and rheology, by which is meant an improvement in the viscoelasticity of one or more of storage modulus G', loss modulus G", and loss tangent tan (δ), or any combination thereof. In a preferred embodiment, the compositions will exhibit a synergistic improvement in transfer resistance, particularly water transfer resistance.

The inventive compositions are contemplated to be synergistic over any range of relative proportions of polyorganosiloxane gum to elastomer based on the observation that cosmetic properties are enhanced due to the combination of a viscous component and an elastic component. Typically, the ratio of silicone polyurethane polymer to polyorganosiloxane gum ranges from about 50:1 to about 1:50, more typically from about 25:1 to about 1:25, and usually from about 10:1 to about 1:10. The synergistic combinations are expected to have their most pronounced effects of the viscoelastic properties of the cosmetic compositions when they are present in a weight ratio of silicone polyurethane polymer to polyorganosiloxane gum from about 5:1 to about 1:5, preferably about 3:1 to about 1:3, and more preferred still from about 2:1 to about 1:2, including a weight ratio of silicone polyurethane polymer to polyorganosiloxane gum of about 1:1.

An essential component of the inventive compositions is a silicone polyurethane polymer. In the broadest sense of the invention, the selection of the silicone polyurethane polymer is not particularly limited and will embrace any polymer comprising organosiloxane units and urethane linkages.

In one embodiment, the silicone polyurethane polymer will be the reaction product of a hydroxyl functionalized polyorganosiloxane, preferably containing two or more hydroxyl groups, with a diisocyantate moiety. The hydroxyl functionalized polyorganosiloxane will typically have the structure of Formula I:

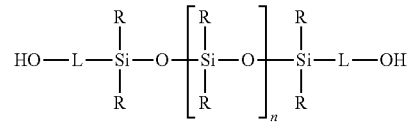

where R is selected independently at each occurrence from hydrogen, hydroxyl, and optionally substituted hydrocarbon groups containing from 1 to 10 carbon atoms, and in particular from optionally substituted alkyl, alkenyl, alkynyl, aryl, alkyl-aryl, or aryl-alkyl groups; preferably R is selected from optionally substituted branched, straight chain, or cyclic $C_{1-6}$ alkyl or alkenyl groups, including without limitation, methyl, ethyl, propyl, isopropyl, butyl, isobutyl, t-butyl, amyl, hexyl, cyclohexyl, vinyl, allyl, and the like or $C_{1-8}$ aryl, alkyl-aryl, or aryl-alkyl groups, including without limitation, phenyl, benzyl, tolyl, xylyl and the like;

wherein each of the foregoing R groups may include optional substitution by one or more heteroatoms, including oxygen, nitrogen, phosphorous, and halogen, particularly fluorine, as exemplified by fluoroalkyl (including perfluoroalkyl) groups, such as mono-, di-, and tri-fluoromethyl, perfluorophenyl, and the like, amino-substituted $C_{1-6}$ alkyl groups, including those having the form $-(CH_2)_{1-6}-NR^N_2$ and $-(CH_2)_{1-6}-NR^N-(CH_2)_{1-6}-N^N_2$ where $R^N$ is typically hydrogen, but may be methyl, ethyl, propyl, and the like; polyether groups including without limitation, polyethyleneoxide groups of the form $-(CH_2CH_2O)_n-$, polypropylene oxide groups of the form $-(CH(CH_3)CH_2O)_n-$ and combinations thereof; and amine oxide, phosphate, hydroxyl, ester, and/or carboxylate functionalities, and the like; or wherein R may comprise an additional group -L-OH;

wherein L either represents a bond or a linker group; preferably L is a linker group selected from divalent hydrocarbons having from 1 to 10 carbon atoms, including divalent alkyl, alkenyl, alkynyl, aryl, alkyl-aryl, or aryl-alkyl groups, as exemplified by $C_{1-10}$ alkyl groups, including without limitation, divalent groups of the form $-(CH_2)_{1-10}-$, preferably $-(CH_2)_{1-6}-$, and more preferably, L is $-CH_2CH_2CH_2-$;

and where n is an integer from 0 to 5,000, preferably from 1 to 200, more preferably from 10 to 100, and more preferred still from 10 to 50. Preferably R represents at least one or more occurrences of methyl, more preferably, R represents methyl at all or substantially all by which is meant that R represents methyl at greater than 90%, 95% or 98% occurrences.

In one embodiment according to the invention, the hydroxyl functionalized polyorganosiloxane comprises a polymethylsiloxane, and suitable has the structure of Formula Ia:

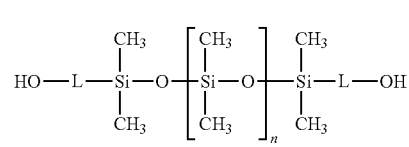

where L and n are as defined previously. In a preferred embodiment of the invention, the hydroxyl functionalized polyorganosiloxane comprises a polymethylsiloxane, and suitable has the structure of Formula Ib:

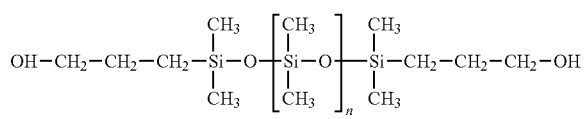

where n is as defined above.

The diisocyanate will be of the form O=C=N—R¹—N=C=O, where $R^1$ is a divalent hydrocarbon group containing from 1 to 20 carbon atoms, including optional substitution with one or more heteroatoms, and in particular $R^1$ will be selected from optionally substituted, branched, straight chain, or cyclic alkyl, alkenyl, alkynyl, aryl, alkyl-aryl, or aryl-alkyl groups; including without limitation:

(i) a group of the form:

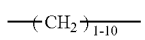

(ii) a group of the form:

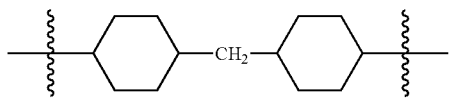

(ii) a group of the form:

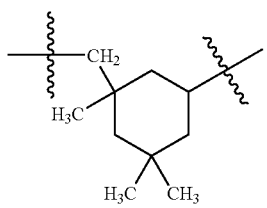

(iv) a group of the form:

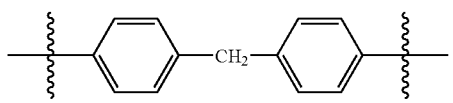

and;
(v) a group of the form:

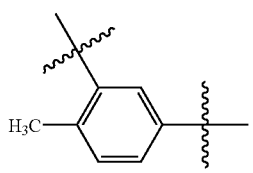

and combinations thereof.

Suitable diisocyanates include, without limitation, toluene diisocyanate; methylene diphenyl diisocyanate, including 2,2'-MDI, 2,4'-MDI, and 4,4'-MDI; 1,6-hexamethylene diisocyanate; isophorone diisocyanate; methylene dicyclohexyl diisocyanate; xylene diisocyanate; cyclohexane diisocyanate; 3,3'-dimethyl-4,4'-diphenylmethane diisocyanate; p-phenylene diisocyanate; m-phenylene diisocyanate; 4,4'-isopropylidene dicyclohexyl isocyanate; and the like. In a preferred embodiment, the diisocyanate is selected from the group consisting of 1,6-hexamethylene diisocyanate, methylene dicyclohexyl diisocyanate, isophorone diisocyanate, and combinations thereof. In one embodiment, the diisocyanate will comprise, consist essentially of, or consist of 1,6-hexamethylene diisocyanate. In another embodiment, the diisocyanate will comprise, consist essentially of, or consist of isophorone diisocyanate. In yet another embodiment, the diisocyanate will comprise, consist essentially of, or consist of methylene dicyclohexyl diisocyanate.

The polyorganosiloxane polyurethane polymer will comprise repeat units derived from the hydroxyl functionalized polyorganosiloxane and the diisocyanate in the form of an AB alternating copolymer, where unit A has the structure of Formula II:

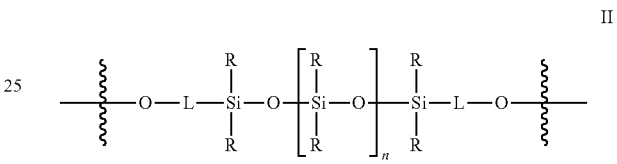

where R, L, and n are as defined previously in relation to Formula I, Ia, and Ib, and where unit B has the structure of Formula III:

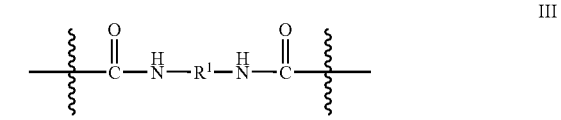

where $R^1$ is as defined previously, and wherein units A and B are arranged in a linear, branched, or cyclic configuration.

When the polymer is a cyclic polymer, it may be represented according to Formula IV:

where z is an integer value from 2 to 2,000. Where the polyorganosiloxane polyurethane polymer is cyclic, the propagation of the polymer is self-terminating. However, in the case of a linear polymer, termination may be accomplished by, for example, allowing the polymerization reaction to run to completion, employing a stoichiometric excess of dihydroxyl polyorganosiloxane of Formula I in relation to diisocyanate, quenching the reaction with a mono-alcohol or an amine, for example a dialkyl amine, including in the reaction mixture quantities of monofunctional reactants, such as mono-hydroxyl polyorganosiloxane analogs of Formula I, and/or mono-functional isocyanate reactants, or any other suitable method for terminating the urethane polymerization reaction. Thus, the polyorganosiloxane polymers may have a variety of terminating groups, including without limitation, hydroxyl groups, including the group -L-OH, tri-alkylsilyl groups, including trimethylsilyl, hydrocarbons, such as linear, branched or cyclic alkyl or aryl groups which may, amines, cabinol, silanols and the like.

The polymer may also include branching or grafting points in the polyorganosiloxane where one or more groups R in Formula I or II is a group such as:

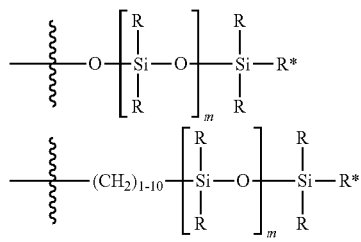

where R is as defined for Formula I, and R* may represent a group -L-O— further coupling the side chain to a unit B of Formula III, which may in turn be further coupled to unit A of Formula II, and so on, or R* may represent -L-OH, a group R, as defined previously, or a terminating group. When the polyorganosiloxane comprises branch or graft points of this type, they may be present as T-type or Q-type branches or grafts, where T denotes that only, one R group on a Si atom is a polyorganosiloxane chain as shown above and Q denotes that both geminal R groups are polyorganosiloxanes. These types of polyorganosiloxane compounds are referred to as T-resin or Q-resin, branched or grafted, co-polymer of polyorganosiloxane polyurethane.

The polyorganosiloxane polyurethane polymers may also be prepared from functionalized isocyanate prepolymers. For example, an isocyanate prepolymer may be a di-functional or multi-functional polyorganosiloxane isocyanate, such as the polyorganosiloxane diisocyanate shown below in Formula V:

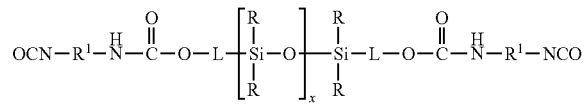

V where R, $R^1$, and L as defined previously and where x is an integer from 0 to 5,000, preferably from 1 to 200, more preferably from 10 to 100, and more preferred still from 10 to 50. The prepolymer may be multi-functional as well by introducing additional isocyanate-bearing groups at one or more R groups. The isocyanate-functionalized polyorganosiloxane prepolymer is reacted with a hydroxyl-functionalized polyorganosiloxane prepolymer such as that according to Formula I or a multi-functional analog thereof. The prepolymer according to Formula V will typically have a molecular weight ranging from about 4,000 to about 15,000 Daltons. The prepolymer according to Formulas I, Ia, and Ib will typically have a molecular weight ranging from about 250 to about 15,000 Daltons.

In one embodiment, the silicone polyurethane polymer free of or is essentially free of polyalkylene glycol subunits, including polyethylene glycol (PEG) or polypropylene glycol (PPG) subunits. By "essentially free of" is meant that the polymer comprises less than about 1% by weight, preferably, less than about 0.5% by weight, and more preferably, less than about 0.1% by weight polyalkylene glycol subunits.

In a currently preferred embodiment, the polyorganosiloxane polyurethane polymer for use in the cosmetic compositions of the invention is a cyclic polymer comprising the reaction product of Formula Ib with a diisocyanate selected from the group consisting of 1,6-hexamethylene diisocyanate, methylene dicyclohexyl diisocyanate, isophorone diisocyanate, and combinations thereof. An exemplary silicone polyurethane polymer is available from Siltech Corporation under the designation MR-20-41. A variety of prepolymers of Formulas I, Ia, and Ib, having varying molecular weights and degrees of functionality, are commercially available from Siltech Corporation under the trade designations "Silmer OH." A variety of prepolymers of Formula V, having varying molecular weights and degrees of functionality, are commercially available from Siltech Corporation under the trade designations "Silmer NCO."

A second essential component of the inventive compositions is an elastomeric material, including without limitation silicone gums, polyisobutylene, natural rubbers, block-copolymer rubbers, and the like. There is essentially no restriction on the nature of the elastomer and any cosmetically suitable elastomer is contemplated to be useful in the practice of the invention.

In one embodiment, the elastomeric material will comprise a siloxane gum, in particular a polyorganosiloxane gum. While it is contemplated that any polyorganosiloxane gum will be suitable in the practice of the invention, the polyorganosiloxane gum will typically have the following general structure:

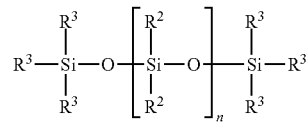

where $R^2$ is selected, independently at each occurrence, from optionally substituted hydrocarbon groups containing from 1 to 10 carbon atoms, and in particular from optionally substituted alkyl, alkenyl, alkynyl, aryl, alkyl-aryl, or aryl-alkyl groups; preferably $R^2$ is selected from optionally substituted branched, straight chain, or cyclic $C_{1-6}$ alkyl or alkenyl groups, including without limitation, methyl, ethyl, propyl, isopropyl, butyl, isobutyl, t-butyl, amyl, hexyl, cyclohexyl, vinyl, allyl, and the like or $C_{1-8}$ aryl, alkyl-aryl, or aryl-alkyl groups, including without limitation, phenyl, benzyl, tolyl, xylyl and the like;

wherein each of the foregoing $R^2$ groups may include optional substitution by one or more heteroatoms, including oxygen, nitrogen, phosphorous, and halogen, particularly fluorine, as exemplified by fluoroalkyl (including perfluoroalkyl) groups, such as mono-, di-, and tri-fluoromethyl, perfluorophenyl, and the like, amino-substituted $C_{1-6}$ alkyl groups, including those having the form —$(CH_2)_{1-6}$—$NR^N_2$ and —$(CH_2)_{1-6}$—$NR^N$—$(CH_2)_{1-6}$—$N^N_2$ where $R^N$ is typically hydrogen, but may be methyl, ethyl, propyl, and the like; polyether groups including without limitation, polyethyleneoxide groups of the form —$(CH_2CH_2O)_n$—, polypropylene oxide groups of the form —$(CH(CH_3)CH_2O)_n$— and combinations thereof; and amine oxide, phosphate, hydroxyl, ester, and/or carboxylate functionalities, and the like;

and optionally wherein $R^2$, at one or more occurrences, may be a group:

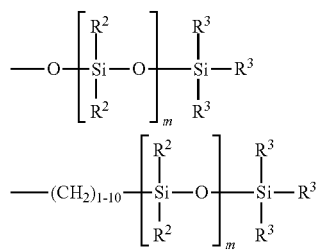

thereby introducing one or more branching points into polyorganosiloxane gum;

and wherein $R^3$ is selected, independently at each occurrence, from hydrogen, hydroxyl, a group —R', or a group —OR'; wherein R' represents optionally substituted hydrocarbon radical having from 1 to 10 carbon atoms, including without limitation alkyl, alkenyl, alkynyl, aryl, alkyl-aryl, or aryl-alkyl groups, and preferably R' is a branched, straight chain, or cyclic $C_{1-6}$ alkyl group, including methyl, ethyl, propyl, isopropyl, butyl, t-butyl, amyl, hexyl, cyclohexyl and the like, optionally comprising one ore more heteroatoms, wherein each of the foregoing groups may include optional substitution by one or more heteroatoms, including oxygen, nitrogen, and halogen, particularly fluorine, as exemplified by fluoroalkyl (including perfluoroalkyl) groups, such as mono-, di-, and tri-fluoromethyl, perfluorophenyl, and the like, and in the case where the one or more heteroatoms include nitrogen, R' may be and amino-substituted $C_{1-6}$ alkyl group, including those having the form —$(CH_2)_{1-6}$—$NR^N{}_2$ and —$(CH_2)_{1-6}$—$NR^N$—$(CH_2)_{1-6}$—$NR^N{}_2$ where $R^N$ is typically hydrogen, but may be methyl, ethyl, propyl, and the like;

and wherein n (and m if present) is an integer value selected to provide a polymer having a viscosity of about 500,000 to about 5,000,000 centistokes at 25° C.

In one embodiment, $R^2$ and $R^3$ are selected from the group consisting of methyl, ethyl, propyl, isopropyl, butyl, isobutyl, t-butyl, amyl, hexyl, and cyclohexyl, vinyl, allyl, phenyl, and combinations thereof. In a preferred embodiment all occurrences of $R^2$ and $R^3$ are methyl groups and the silicone gum is a polydimethylsiloxane (dimethicone). A representative polydimethylsiloxane silicone gum has the structure shown in Formula VI:

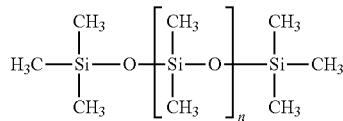

VI

The polyorganosiloxane elastomeric material may include combinations of low molecular weight polymers (i.e., fluids), high molecular weight polymers (i.e., gums), and highly cross-linked silicones (i.e., resins). Combinations of the foregoing are suitable provided that the polyorganosiloxane material exhibit elastomeric properties characteristic of gums, i.e., the G' storage modulus does not break down over a wide range of shear rates. These properties are enhanced where the polyorganosiloxane gum has a viscosity of from about 1,000,000 centistokes to about 3,500,000 centistokes when measure at 25° C. In a representative embodiment, the polyorganosiloxane gum has a viscosity of about 2,500,000 centistokes at 25° C. An example of suitable commercially available polyorganosiloxane gum is SE63 dimethicone gum from GE Silicones.

Other elastomers found to be suitable for inclusion in the inventive compositions include polyolefin polymer, including without limitation, polyisobutylenes. Polyisobutylenes may be prepared by cationic polymerization of isobutylene and will comprise repeat units as shown below:

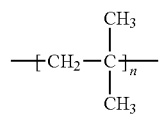

These polymers are preferably, but not necessarily, fully saturated to impart chemical stability. Depending on the value of n, polyisobutylenes may range from a liquid to a rubber as the molecular weight is increased. At low molecular weight, such as below 5,000 Daltons the polymers tend to be liquid and at higher molecular weight, for example, greater than 100,000 Daltons, they tend to be rubbers. One suitable polyisobutylene is Permethyl 98B from Presperse, Inc. which case the chemical abstracts number CAS:9003-29-6.

The elastomer component may include a natural rubber such as the latex obtained from the *Hevea brasiliensis* tree. Such natural rubbers comprise primarily cis-1,4-polyisoprene repeat units of the form:

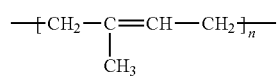

These rubbers are typically characterized by a low glass transition temperature ($T_g$~–70° C.) and a high shear storage plateau modulus. The molecular weight of these natural rubbers is very high, typically greater than 1,000,000 Daltons.

Synthetic rubbers are also contemplated to by useful elastomeric components. Synthetic rubbers include thermoplastic block copolymers rubbers such as ABA block copolymers where A is polystyrene block of the form and B is as polydiene, such as, for example, polyisoprene and/or polybutadiene, as shown below:

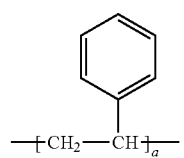

A

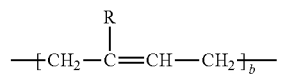

B

In the case where R in unit B is hydrogen, the polydiene block is a polybutadiene and the resultant block co-polymer with polystyrene is referred to in the art as an SBS copolymer. In the case where R is methyl, the polydiene is polyisoprene and the block co-polymer with polystyrene is referred to in the art as an SIS copolymer. The molecular weight of the block copolymers is typically on the order of 100,000 to 200,000 Daltons. It is contemplated the SBS and SIS copolymers will be suitable elastomers for use in the inventive compositions. In these polymers, the polystyrene is typically present from about 10 to about 20% by weight of the rubber. As the minor component, the polystyrene block is believed to phase separate into microscopic spherical domains that act as cross-links at each end of a polydiene polymer chain. These polystyrene component is typically glassy at room temperature ($T_g$~100° C.) whereas the polydiene component is rubbery ($T_g$~—70° C.). The interesting elastic properties of these block copolymers arising as a result of the polydiene chains being anchored in the glassy polystyrene domain, thus the block copolymers behave as cross-linked rubbers. At temperatures above $T_g$ of the polystyrene, the microscopic glassy domains melt allowing the polymer chains to flow, permitting hot-melt processing. All of those foregoing properties are expected to impart unique rheological attributes to cosmetic formulations comprising these materials, and in particular they are contemplated to enhance the viscoelastic properties of the cosmetic in a synergistic manner in combination with a polyorganosiloxane polyurethane polymers. Suitable block copolymers include, without limitation, those available from Shell Chemical under the tradename Kraton™ adhesives.

The cosmetic compositions will typically comprise a cosmetically acceptable vehicle. By "cosmetically acceptable" is meant that the vehicle is safe for contact with human skin and the like. It is contemplated that any cosmetically acceptable vehicle known in the art will be useful. The vehicle may comprise water, hydrophobic, and/or hydrophilic solvents. Suitable hydrophilic solvents include but are not limited to, butylene glycol, propylene glycol, pentylene glycol, caprylyl glycol, polyglycerol diisostearate, dimethylsiloxane/glycol copolymer, isopropyl myristate, triisostearyl citrate, or any combinations thereof. Suitable hydrophobic vehicles include hydrocarbon oils, which may be saturated or unsaturated, have an aliphatic character and be straight or branched chained or contain alicyclic or aromatic rings. Examples of preferred non-polar, volatile hydrocarbons include polydecanes such as isododecane and isodecane, including for example, Permethyl-99A (Presperse Inc.) and the $C_7$-$C_8$ through $C_{12}$-$C_{15}$ isoparaffins such as the Isopar Series available from Exxon Chemicals. A representative solvent is isododecane. Silicone oils are also contemplated to be suitable vehicles, including without limitation hexameihyldisiloxane (HMDS), polydimethylsiloxane (dimethicone) polymers, and cyclodimethicones. Suitable dimethicone polymers are available from Dow Corning under the name Dow Corning 200® Fluid and have viscosities ranging from 0.65 to 600,000 centistokes. Suitable non-polar, volatile liquid silicone oils are disclosed in U.S. Pat. No. 4,781,917, herein incorporated by reference in its entirety. Additional volatile silicones materials are described in Todd et al., "Volatile Silicone Fluids for Cosmetics", Cosmetics and Toiletries, 91:27-32 (1976), herein incorporated by reference in its entirety. Linear volatile silicones generally have a viscosity of less than about 5 centistokes at 25° C., whereas the cyclic silicones have viscosities of less than about 10 centistokes at 25° C. Examples of cyclomethicones of varying viscosities include Dow Corning 200, Dow Corning 244, Dow Corning 245, Dow Corning 344, and Dow Corning 345, (Dow Corning Corp.); SF-1204 and SF-1202 Silicone Fluids (G.E. Silicones), GE 7207 and 7158 (General Electric Co.); and SWS-03314 (SWS Silicones Corp.). Polyethersiloxane copolymers are also contemplated as useful vehicles including, without limitation, polyoxyalkylene ether copolymers having a viscosity of about 1200 to 1500 centistokes at 25° C., including for example SF1066 organosilicone surfactant (General Electric Company).

The combination of silicone polyurethane and elastomer will typically comprise from about 0.1% by weight to about 90% by weight of the total cosmetic composition. More typically, the combination will comprise about 1% by weight to about 60% by weight and preferably will comprise from about 5% by weight to about 50% by weight of the total cosmetic composition.

The carrier will typically comprise from about 5% to about 95% by weight of the composition, and more typically between about 30% and about 80% by weight. In preferred embodiments, the carrier comprises between about 50% and about 70% by weight of the composition.

The compositions according to the invention may be useful in a variety of cosmetic and personal care products, including without limitation, lipsticks, and lipcolors, lip gloss, mascaras, transfer-resistant foundations, eyeliner, eyeshadow, water-proof sunscreens and insect repellents, skin care products, hair care products, antiperspirants and deodorants, and other cosmetic products where durable, transfer resistant films are desired.

Where the product is a color cosmetic, such as a lipstick, lip gloss, nail enamel, mascara, foundation, and the like, the compositions will further comprise one or more coloring agents. It is within the skill in the art to choose coloring agents and combinations of coloring agents to produce a desired color. Suitable coloring agents, including pigments, lakes, and dyes, are well known in the art and are disclosed in the C.T.F.A. Cosmetic Ingredient Handbook, First Edition, 1988, the contents or which are hereby incorporated by reference. Organic pigments include, for example, FD&C dyes, D&C dyes, including D&C Red, Nos. 2, 5, 6, 7, 10, 11, 12, 13, 30 and 34, D&C Yellow No. 5, Blue No. 1, Violet No. 2. Exemplary inorganic pigments include, but are not limited to, metal oxides and metal hydroxides such as magnesium oxide, magnesium hydroxide, calcium oxide, calcium hydroxides, aluminum oxide, aluminum hydroxide, iron oxides ($\alpha$-$Fe_2O_3$, y-$Fe_2O_3$, $Fe_3O_4$, FeO), red iron oxide, yellow iron oxide, black iron oxide, iron hydroxides, titanium dioxide, titanium lower oxides, zirconium oxides, chromium oxides, chromium hydroxides, manganese oxides, cobalt oxides, cerium oxides, nickel oxides and zinc oxides and composite oxides and composite hydroxides such as iron titanate, cobalt titanate and cobalt aluminate. Other suitable colorants include ultramarine blue (i.e., sodium aluminum silicate containing sulfur), Prussian blue, manganese violet, bismuth oxychloride, talc, mica, sericite, magnesium carbonate, calcium carbonate, magnesium silicate, aluminum magnesium silicate, silica, titanated mica, iron oxide titanated mica, bismuth oxychloride, and the like. The colorants may be surface modified with, for example, fluoropolymers, to adjust one or more characteristics of the colorant as described in, for example, U.S. Pat. Nos. 6,471,950, 5,482,547, and 4,832,944, the contents of which are hereby incorporated by reference. Suitable pearling pigments include without limitation bismuth oxychloride, guanine and titanium composite materials containing, as a titanium component, titanium dioxide, titanium lower oxides or titanium oxynitride, as disclosed in U.S. Pat. No. 5,340,569, the contents of which are hereby incorporated by reference. The compositions may also include glittering agents.

Various fillers and additional components may be added. Suitable fillers include without limitation silica, treated silica, talc, zinc stearate, mica, kaolin, Nylon powders such as Orgasol™, polyethylene powder, Teflon™, starch, boron nitride, copolymer microspheres such as Expancel™ (Nobel Industries), Polytrap™ (Dow Corning) and silicone resin microbeads (Tospearl™ from Toshiba), and the like. Functional agents may be, for example, insect repellants, UV absorbers, UV blockers, antiperspirants, moisturizers, conditioners, tooth whiteners, and the like.

Additional pigment/powder fillers include, but are not limited to, inorganic powders such as gums, chalk, Fuller's earth, kaolin, sericite, muscovite, phlogopite, synthetic mica, lepidolite, biotite, lithia mica, vermiculite, aluminum silicate, starch, smectite clays, alkyl and/or trialkyl aryl ammonium smectites, chemically modified magnesium aluminum silicate, organically modified montmorillonite clay, hydrated aluminum silicate, fumed aluminum starch octenyl succinate barium silicate, calcium silicate, magnesium silicate, strontium silicate, metal tungstate, magnesium, silica alumina, zeolite, barium sulfate, calcined calcium sulfate (calcined gypsum), calcium phosphate, fluorine apatite, hydroxyapatite, ceramic powder, metallic soap (zinc stearate, magnesium stearate, zinc myristate, calcium palmitate, and aluminum stearate), colloidal silicone dioxide, and boron nitride; organic powder such as polyamide resin powder (nylon powder), cyclodextrin, methyl polymethacrylate powder, copolymer powder of styrene and acrylic acid, benzoguanamine resin powder, poly(ethylene tetrafluoride) powder, and carboxyvinyl polymer, cellulose powder such as hydroxyethyl cellulose and sodium carboxymethyl cellulose, ethylene glycol monostearate; inorganic white pigments such as magnesium oxide; and stabilizers/rheology modifiers, for example, Bentone Gel and Rheopearl TT2. Other useful powders are disclosed in U.S. Pat. No. 5,688,831, the disclosure of which is hereby incorporated by reference.

In another embodiment, the invention is formulated in a conventional lipstick or lipcolor product. Such conventional lip products include, without limitation, U.S. Pat. Nos. 6,509,009, 6,428,797, 6,261,576, 5,747,017, 5,318,775, and 4,935,228, the disclosures of which are hereby incorporated by reference.

The compositions according to the invention may include viscosity modifying materials, structuring agents, synthetic or natural waxes, film-forming agents, preservatives, stabilizing agents, flavors, and fragrances. The compositions of the invention may optionally comprise other active and inactive ingredients typically associated with any of the foregoing cosmetic and personal care products, including, but not limited to, excipients, fillers, emulsifying agents, antioxidants, surfactants, film formers, chelating agents, gelling agents, thickeners, emollients, humectants, moisturizers, vitamins, minerals, viscosity and/or rheology modifiers, sunscreens, keratolytics, depigmenting agents, retinoids, hormonal compounds, alpha-hydroxy acids, alpha-keto acids, anti-mycobacterial agents, antifungal agents, antimicrobials, antivirals, analgesics, lipidic compounds, anti-allergenic agents, H1 or H2 antihistamines, anti-inflammatory agents, anti-irritants, antineoplastics, immune system boosting agents, immune system suppressing agents, anti-acne agents, anesthetics, antiseptics, insect repellents, skin cooling compounds, skin protectants, skin penetration enhancers, exfollients, lubricants, fragrances, colorants, staining agents, depigmenting agents, hypopigmenting agents, preservatives, stabilizers, pharmaceutical agents, photostabilizing agents, and mixtures thereof. In addition to the foregoing, the personal care products of the invention may contain any other compound for the treatment of skin disorders.

The composition according to the invention is expected to achieve improved durability and/or transfer resistance and remain on the skin or hair for a long-wear period such as from about 1 to about 24 hours. The composition is also expected to maintain transfer resistance and/or long-wear properties for a long-wear period such as from about 1 hour to about 24 hours. Typically, a long-wear period may be from about 8 to about 24 hours. Preferably, the long-wear period may be from about 8 to about 12 hours. An alternative preferred long-wear period may be from about 12 to about 24 hours.

A variety of evaluation methods of transfer resistance and long wearing properties are known in the cosmetic arts, such as in dry blot, oil blot, and rub tests. For example, U.S. Pat. No. 6,071,503 discloses various methods of evaluating cosmetic properties, the disclosure of which is hereby incorporated by reference.

Improved Cosmetic Properties

The combination of a silicone polyurethane polymer and an elastomer in a cosmetic formulation provides synergistic results in cosmetic properties, particularly, substantivity or adhesive strength, of the cosmetic formulation to a selected surface. The flow and deformation behaviors of the lip gloss formulation directly affects its long wearing, transfer resistant properties. The polyorganosiloxane polyurethane polymers are, by nature, viscous materials whereas elastomers are, by definition, highly elastic. The synergistic combination of the present invention includes an elastic component from the elastomers to balance the viscosity of the polyorganosiloxane polyurethane polymer. As discussed below, it is believed that balanced viscoelasticity of the lip gloss formulation provides improved substantivity to the skin and thus will contribute to long-wear, flexibility, and transfer resistance of the lip gloss formulation under both oily and watery conditions.

Balanced viscoelastic properties are expected to improve transfer resistance and provide good substantivity to the lip gloss formulation. Increased elasticity provide for improved transfer resistance of the lip gloss formulation, but as the elasticity increases, the polymeric chains of the material becomes more entangled resulting in a loss of adhesion to the surface. Viscosity is related to the glass transition temperature ($T_g$) of a material through the well-known Williams-Landel-Ferry (WLF) equation. As viscosity increases, the glass transition temperature ($T_g$) also increases. An increase in the glass transition temperature ($T_g$) results in a more brittle cosmetic product, particularly where $T_g$ is above temperatures typically encountered by a cosmetic product (e.g., room temperature or body temperature). A decreased viscosity provides a lower glass transition temperature ($T_g$) and a more adhesive, but more transferable material at temperatures typically encountered by a cosmetic product. The viscoelastic properties may be quantified on the basis of storage modulus G', loss modulus G", and loss tangent tan (δ) which is the ratio of G"/G'.

In general, a material can respond to shear force by (1) storing recoverable elastic energy or (2) dissipating unrecoverable viscous loss. The storage modulus (G') quantifies elastic behavior and reveals the ability of the polymer system to store elastic energy associated with recoverable elastic deformation while the loss modulus (G") measures the dynamic viscous behavior that relates to the dissipation of energy associated with unrecoverable viscous loss. The loss tangent (tan δ), which is the ratio of the loss modulus to the storage modulus, compares the ratio of energy lost to energy stored in a cycle of deformation and provides a comparative parameter that combines both the elastic and the viscous contributions the system (i.e., viscoelasticity). The relationship between G', G" and tan δ is:

$$\tan\delta = \frac{G''}{G'}$$

Lip gloss formulations typically encounter low levels of shear forces during wear. It would be particularly desirable to impart improved transfer resistance and good substantivity to lip gloss formulations at shear rates typically experienced during wear, such as from about 0.1 to about 1 sec$^{-1}$. Preferably, the lip gloss formulations may demonstrate improved transfer resistance and good substantivity at shear rates from about 0.1 to about 2.5 sec$^{-1}$. More preferably, the lip gloss formulations may demonstrate improved transfer resistance and good substantivity at shear rates from about 0.1 to about 5 sec$^{-1}$. Even more preferably, the lip gloss formulations may demonstrate improved transfer resistance and good substantivity at shear rates from about 0.1 to about 10 sec$^{-1}$. Most preferably, the lip gloss formulations may demonstrate improved transfer resistance and good substantivity at shear rates from about 0.1 to about 15 sec$^{-1}$.

Lip gloss formulations typically encounter higher levels of shear stress during application to the skin. At higher shear rates, it is particularly preferable that the lip gloss formulation becomes more deformable so that a consumer may readily apply and spread the lip gloss formulation to cover a selected surface. Accordingly, it is particularly desirable for the lip gloss formulation to become more viscous at shear rates typically encountered during application to the skin, for example, shear rates from about 1 sec$^{-1}$ to about 100 sec$^{-1}$. Preferably, the lip gloss formulation becomes more viscous at shear rates from about 2.5 sec$^{-1}$ to about 90 sec$^{-1}$. More preferably, the lip gloss formulation becomes more viscous at shear rates from about 5 sec$^{-1}$ to about 80 sec$^{-1}$. Most preferably, the lip gloss formulation becomes more viscous at shear rates from about 10 sec$^{-1}$ to about 70 sec$^{-1}$.

The viscoelastic properties may be characterized, for example, by a loss tangent, tan(δ) which is substantially linear or smooth over the widest possible range of shear rates, but exhibits a sharp, discontinuous rise at shear rates typically encountered during application to a selected surface. In addition, at shear rates typically encountered during wear, the lip gloss formulation exhibits balanced viscoelastic properties, for example, having a loss tangent value within a range from about 1 to about 10. The loss tangent may be substantially linear or smooth and have a value between about 1 to about 10 at shear rates from about 0.1 to about 15 sec$^{-1}$, preferably from about 0.1 to about 20 sec$^{-1}$, more preferably from about 0.1 to about 30 sec$^{-1}$, and more preferred still, from about 0.1 to about 70 sec$^{-1}$. By "substantially linear or smooth" is meant that the curve of G', G", or tan(δ) versus shear rate do not exhibit a sharp, discontinuous rise or fall over a given range of shear rates.

EXAMPLE I

Lip Gloss

A long-wearing, transfer resistant lip gloss having a synergistic combination of silicone polyurethane polymer and silicone gum elastomer is provided in Table 1. The lip gloss may be used alone as a long-wearing transfer resistant lip gloss, or as a base coat under a clear or tinted top coat. An optional top coat formulation is also provided in Table 1. The optional top coat may be employed to enhance shine and/or moisturization without substantially removing the base coat.

TABLE 1

| Components | Weight % |
|---|---|
| Silicone Polyurethane MR-20-41(Siltech Corporation) (40% in IDD) | 45.00 |
| Silicone Gum SE63 (GE Silicones)/IDD (1:2) | 10.00 |
| Bentone Gel - IDD/disterardimonium | 4.00 |
| Pentaerythrityl Tetra-Di-T-Butyl Hydroxyhydrocinnamate | 0.05 |
| Cromapure GDE | 1.00 |
| Caprylyl Glycol | 0.50 |
| Fragrance/Acrylate Copolymer | 0.20 |
| Pigment Blend | 11.40 |
| Isododecane | 27.85 |
| Total | 100 |
| Optional Top Coat | |
| Polybutene (film former, shine, thickener) | 70.00 |
| Hydrogenated Polyisobutene (oil/solvent) | 26.43 |
| *Jojoba* Oil/Gellants/BHT-Hi Viscosity (moisturizer, shine, thickener) | 3.00 |
| Hydroxystearic Acid (gelling agent) | 0.27 |
| Benzoic Acid (preservative) | 0.20 |
| Fragrance (optional) | 0.10 |
| Total | 100 |

EXAMPLE II

The effect of adding silicone gum to a lip gloss formulation containing a silicone polyurethane copolymer was investigated in relation to the transfer resistance of a lip product. Two samples of a lip gloss formulation were prepared according to Table 2.

The silicone polyurethane polymer is a commercial product sold under the designation MR-20-41 (Siltech Corporation), which is available as a solution in IDD at about 40% by weight. Similarly, the silicone gum is a commercial product sold under the trade name SE63 (GE Silicones) and available as a solution in IDD at about 50% by weight. Table 2 below provides the converted weights representing the weight % of neat silicone polyurethane copolymer and neat silicone gum in each sample formulation (i.e., in the absence of IDD).

TABLE 2

| | Sample Number: | |
|---|---|---|
| | 1 | 2 |
| Components | Weight % | |
| Silicone Polyurethane MR-20-41 (Siltech Corp.) | 15.0 | 15.0 |
| Silicone Gum SE63 (GE Silicones) | — | 8 |
| Rhoepearl TT2 | 2 | 2 |
| Pigment Blend | 10 | 10 |
| Isododecane | q.s. | q.s. |
| Total | 100 | 100 |

The water and oil transfer resistances of the lip gloss formulations of Samples 1 and 2 were examined in comparison to the commercial lip coloring products Lipfinity™ (Procter & Gamble) and Lip Polish™ (Maybelline) using a modification of the transfer resistance testing protocol of U.S. Pat. No. 6,074,654, the disclosure of which is hereby incorporated by reference. The testing protocol is described below.

Transfer Resistance Test Method

This method may be utilized to determine the water and oil transfer resistances and adhesion properties of a cosmetic film. This test predicts the ability of a cosmetic film to resist color transfer to objects contacting the skin. Such objects include clothing, handkerchiefs or tissues, napkins and implements such as cups, glasses and table wear, and oily fingers or objects such as oily foods.

Films formed from cosmetic compositions exhibit a degree of transfer resistance directly proportional to the hardness and solvent-resistance of the film. The hardness and solvent-resistance may be expressed as a function of the blot and rub test as described below.

Equipment:
(1) Glass plates;
(2) Collagen sausage casing such as Nippi Casing F Grade;
(3) Constant humidity chamber adjusted to 95% relative humidity;
(4) Utility Knife;
(5) Ruler;
(6) Single-sided adhesive tape;
(7) Double-sided adhesive tape;
(8) 25 micron thickness slot draw-down bar;
(9) White Styrofoam dinner plate such as Amoco Selectables™ Plastic DL® Tableware;
(10) 1.5 inch diameter circular metal punch;
(11) 1 kilogram weight;
(12) Vegetable oil;
(13) Brush-tip cosmetic applicator; and
(14) Lint-Free Wiper, such as Kimwipes® EX-L.

Procedure:
(1) Prepare a 3×4 inch sheet of collagen sausage casing by hydrating it in a 90% relative humidity chamber for at least 24 hours;
(2) Remove the collagen sheet to ambient conditions and immediately wrap tightly around the glass plate. Attach the collagen sheet to the glass using adhesive tape. The collagen surface should be flat and free of wrinkles;
(3) Allow the collagen-wrapped slide to equilibrate at ambient conditions for about 24 hours;
(4) Apply thin (1 mm), uniform films of a sample cosmetic composition on the collagen;
(5) Allow the cosmetic samples on the collagen surface to rest at ambient conditions for about one hour;
(6) Using a pipette, drop three drops of vegetable oil onto samples located the right side of the collagen surface. Using another pipet, drop three drops of water onto the left side of the collagen surface. Samples on the right side are used to determine the oil transfer resistance while samples on the left side are used to determine the water transfer resistance of the sample cosmetic composition;
(7) Separately for the oil and water sections, distribute the oil or water evenly over the surface of each cosmetic film sample using cosmetic brush applicators, brushing lightly;
(8) Allow the solvent to remain on the film undisturbed for about 15 minutes;
(9) Using a lint-free wiper, carefully blot excess solvent from the surface of each cosmetic film sample. Apply as little pressure as possible during this step;
(10) Cut two disks from a clean, white Styrofoam dinner plate using a 1.5 inch diameter circular punch. The surface and edges of each disk should be smooth and even;
(11) Firmly attach with double-sided adhesive tape each disk from step (10) to the bottom surface of a 1 kg weight;
(12) Set the weight on top of the cosmetic samples applied to the collagen surface from step (5) above so that a first disk is in contact with the oil section of the film (i.e., the right side of the collagen surface) and a second disk is in contact with the water section of the film (i.e., the left side of the collagen surface). It is important to position the weight gently so that excess force beyond 1 kg is not applied;
(13) Grasping the top of the 1 kg weight, carefully rotate each disk through 360 degrees while maintaining the 1 kg force on the film. Do not lift or press the weight into the film during the rotating motion to the weight. The entire 360 degree rotation is preferably completed within a time interval between 3 and 5 seconds;
(14) Lift the weight straight up off the film surface and carefully remove the disk from the weight avoiding damage to the disk;
(15) Color transfer on each disk is visually assessed by comparing disks obtained using commercial products. The commercial products serve as positive and negative control benchmarks. The positive control is the Lipfinity™ product and the negative control is the Lip Polish™ product; and
(16) The criteria used in the "Star Grading System" for measuring the degree of transfer is shown in Table 3.

TABLE 3

| Star Grading System | |
|---|---|
| Visual Assessment of Transfer | Scale |
| Less than Negative Control | * (1) |
| Equal to or slight better than Negative control | ** (2) |
| Between Negative and Positive Control | *** (3) |
| About equal to positive control | **** (4) |
| Better than positive control | ***** (5) |

The results indicate that the lip gloss formulations of Example I exhibit equal or better water and oil transfer resistances than the negative (Lip Polish™) control. However, only Sample 2 exhibits equal or better water and oil transfer resistances than the positive (Lipfinity™) control. The results are quantified on the basis of the Star Grading System as shown below in Table 4.

TABLE 4

| | Transfer Resistance Properties | |
|---|---|---|
| | Water | Oil |
| Sample Number: | Transfer Resistance (Star Grading) | Transfer Resistance (Star Grading) |
| 1 | 2 | 3 |
| 2 | 5 | 4 |

The results indicate that the combination of silicone polyurethane and silicone gum (Sample 1) is superior in water and oil transfer resistance as compared to silicone polyurethane copolymer alone (Sample 2). Notably, the addition of silicone gum in Sample 2 resulted in a marked improved water and oil transfer resistance over Sample 1.

EXAMPLE III

Based on the results described in Example II, Samples 3 through 10 were prepared to investigate the synergistic properties of silicone polyurethane copolymer and elastomeric materials (e.g., silicone gum and/or polyisobutylene). Sample 3 comprises silicone polyurethane in the absence of elastomers whereas Samples 4 and 5 comprise the two elastomers in the absence of a silicone polyurethane. Samples 6 through 10 comprise various combinations of silicone polyurethane and elastomers.

The silicone polyurethane is a commercially available product sold under the designation MR-20-41 (Siltech Corporation), which is available in IDD at about 40% by weight. Similarly, the silicone gum SE63 (GE Silicones) is also available in IDD at about 33% by weight. Further, the polyisobutylene is commercially sold under the designation Permethyl 98B (Presperse, Inc.) and available as a 50% solution in IDD. Table 5 below provides the converted weights representing the weight % of neat silicone polyurethane copolymer, neat silicone gum, and/or neat polyisobutylene in each sample formulation (i.e., in the absence of IDD).

TABLE 5

| Components | Sample Number: | | | | | | | |
|---|---|---|---|---|---|---|---|---|
| | 3 | 4 | 5 | 6 | 7 | 8 | 9 | 10 |
| | Weight % | | | | | | | |
| Silicone Polyurethane MR-20-41 (Siltech Corp.) | 18.00 | — | — | 12.00 | 12.00 | 6.00 | 12.00 | 6.00 |
| Silicone Gum SE 63 (GE Silicones) | — | 18.00 | — | 6.00 | — | 6.00 | 3.00 | 12.00 |
| Permethyl 98B (Presperse, Inc.) | — | — | 18.00 | — | 6.00 | 6.00 | 3.00 | — |
| Caprylyl Glycol | 0.50 | 0.50 | 0.40 | 0.50 | 0.50 | 0.50 | 0.50 | 0.50 |
| Tinoguard | 0.05 | 0.05 | 0.05 | 0.05 | 0.05 | 0.05 | 0.05 | 0.05 |
| Bentone Gel | 10.00 | 10.00 | 10.00 | 10.00 | 10.00 | 10.00 | 10.00 | 10.00 |
| Pigment | 10.00 | 10.00 | 10.00 | 10.00 | 10.00 | 10.00 | 10.00 | 10.00 |
| Isododecane | q.s. | q.s. | q.s. | q.s. | q.s. | q.s. | q.s. | q.s. |
| Total | 100.00 | 100.00 | 100.00 | 100.00 | 100.00 | 100.00 | 100.00 | 100.00 |

It was observed that the lip gloss formulation having 18% by weight silicone polyurethane copolymer in the absence of any elastomer (i.e., Sample 3) was a relatively unstable formulation and demonstrated phase separation. To minimize the potential for experimental error (i.e., phase separation of the formulation biasing the measurements obtained using the transfer resistance test) and to improve the reliability of the results, two identical samples (Samples 3A and 3B) of this formulation were prepared.

In contrast to what was observed for Sample 1 of Example II, Sample 3A provided relatively high oil transfer resistance, showing a Star Grading of 4, but provided an unusually high water transfer resistance, giving a Star Grading of 5. It is believed that this result is spurious as phase separation was clearly visible in Sample 3A prior to transfer resistance measurements, which compromised the accuracy and reliability of the transfer resistance test. Measurements generated using Sample 3A were, therefore, discarded.

The remainder of the measurements were conducted using Sample 3B, which did not suffer from phase separation. The water and oil transfer resistance test was repeated nine times for Sample 3B. The nine water transfer resistance tests yielded of 2, five measurements of 3 and one measurement of 4 on the Star Grading System. The nine oil transfer resistance tests gave two measurements of 3, five measurements of 4 and two measurements of 5. The transfer resistance data for Sample 3, as shown in Table 6 and discussed below, is represented by the mean transfer resistance of the nine tests of Sample 3B.

The water and oil transfer resistance properties of Samples 4 through 10 were also obtained using the method described in Example II. These samples did not visibly show any phase separation during the transfer resistance tests. The results for Samples 4 through 10 are quantified on the basis of the Star Grading System as shown below in Table 6.

TABLE 6

| | Transfer Resistance Properties | |
|---|---|---|
| Sample Number: | Water Transfer Resistance (Star Grading) | Oil Transfer Resistance (Star Grading) |
| 3[1] | 2.8 | 4 |
| 4 | 4 | 1 |
| 5 | 1 | 2 |
| 6 | 5 | 5 |
| 7 | 3 | 5 |
| 8 | 5 | 4 |
| 9 | 5 | 5 |
| 10 | 5 | 3 |

[1]Sample 3 is represented by the average Star Grading value of the 9 transfer resistance tests for Sample 3B.

The results indicate that silicone polyurethane polymer and silicone gum in lip gloss formulations act synergistically to impart water transfer resistance. As shown in Table 6, the combination of silicone polyurethane and silicone gum in Samples 6 and 10 are superior on the basis of water transfer resistance to both Samples 3 and 4, which do not include this synergistic combination. Both Samples 6 and 10 provide a Star Grading of 5 for water transfer resistance whereas Sample 3 shows an inferior Star Grading of 2.8 and Sample 4 shows a modestly inferior Star Grading of 4 for water transfer resistance.

The results also demonstrate that the combination of silicone polyurethane polymer, silicone gum, and polyisobutylene synergistically improves water transfer resistance. As shown in Table 6, Samples 8 and 9 were found to be superior on the basis of water transfer resistance to Samples 3, 4 and 5, which do not include this synergistic combination. Both Samples 8 and 9 exhibit the Star Grading of 5 for water transfer resistance whereas Sample 3, 4, and 5 show inferior Star Gradings of 2.8, 4 and 1, respectively.

The results also clearly show that silicone polyurethane polymer and polyisobutylene in lip gloss formulations act synergistically to impart oil transfer resistance. Sample 7 which comprises a combination of silicone polyurethane and polyisobutylene gives superior oil transfer resistance as compared to Sample 3, which comprises silicone polyurethane but no elastomer, and Sample 5, which comprises polyisobutylene but no silicone polyurethane. Notably, Sample 7 provides a superior Star Grading of 5 for oil transfer resistance as compared to the oil transfer resistance of Samples 3 and 5.

During normal wear conditions, a lip gloss formulation may be exposed to both aqueous and oily conditions. Often, the lip gloss formulation may be exposed to both water and oil at or about the same time, such as, for example, during the consumption of food and beverage. To predict the overall ability of a cosmetic film to resist color transfer to objects contacting the skin under normal wear conditions, which includes exposure to both water and oil, lip gloss formulations may also be evaluated using a parameter for combined transfer resistance, which is defined by the sum of the water transfer resistance and the oil transfer resistance of each sample.

The combined transfer resistance of Samples 3 through 10 were obtained by summing the water transfer resistance and the oil transfer resistance of each sample. The combined transfer resistance for Sample 3 was obtained by the sum of the average water transfer resistance and the average oil transfer resistance of nine transfer resistance tests described previously. The combined transfer resistance for Samples 3 through 10 are provided on the basis of the Star Grading System as shown below in Table 7.

TABLE 7

| Sample Number: | Combined Transfer Resistance |
|---|---|
| 3[1] | 6.8 |
| 4 | 5 |
| 5 | 3 |
| 6 | 10 |
| 7 | 8 |
| 8 | 9 |
| 9 | 10 |
| 10 | 8 |

[1]Sample 3 is represented by the average Star Grading value of 9 transfer resistance tests for Sample 3B.

The results show that the combination of silicone polyurethane polymer and elastomer in a lip gloss formulation synergistically imparts transfer resistance based on the combined transfer resistance parameter. As shown in Table 7, Samples 6 through 10, which comprises a combination of silicone polyurethane with at least one elastomer, exhibit overall superiority based on the combined transfer resistance as compared to Samples 3, 4 and 5, which do not include such combination.

EXAMPLE IV

Samples 11 through 17 were prepared to investigate the effect of different amounts of silicone polyurethane on the transfer resistance of a lip product. The silicone polyurethane polymer for Samples 11 through 17 is the same as the silicone polyurethane polymer listed in Example III, which is a commercial product sold under the designation MR-20-41 (Siltech Corporation) and available as a solution in IDD at about 60% by weight. Table 8 below provides the converted weights representing the weight % of neat silicone polyurethane copolymer in each sample formulation (i.e., in the absence of IDD).

TABLE 8

| | Sample Number: | | | | | | | |
|---|---|---|---|---|---|---|---|---|
| Components | 3 | 11 | 12 | 13 | 14 | 15 | 16 | 17 |
| | Weight % | | | | | | | |
| Silicone Polyurethane MR-20-41 (Siltech Corp.) | 18.00 | 16.00 | 14.00 | 12.00 | 10.00 | 8.00 | 6.00 | 4.00 |
| Silicone Gum SE 63 (GE Silicones) | — | — | — | — | — | — | — | — |
| Permethyl 98B (Presperse, Inc.) | — | — | — | — | — | — | — | — |
| Caprylyl Glycol | 0.50 | 0.50 | 0.50 | 0.50 | 0.50 | 0.50 | 0.50 | 0.50 |
| Tinoguard | 0.05 | 0.05 | 0.05 | 0.05 | 0.05 | 0.05 | 0.05 | 0.05 |
| Bentone Gel | 10.00 | 10.00 | 10.00 | 10.00 | 10.00 | 10.00 | 10.00 | 10.00 |
| Pigment | 10.00 | 10.00 | 10.00 | 10.00 | 10.00 | 10.00 | 10.00 | 10.00 |
| Isododecane | q.s. | q.s. | q.s. | q.s. | q.s. | q.s. | q.s. | q.s. |
| Total | 100.00 | 100.00 | 100.00 | 100.00 | 100.00 | 100.00 | 100.00 | 100.00 |

The water and oil transfer resistance properties were obtained using the method described in Example II. These samples also did not visibly show any phase separation during the transfer resistance tests. The combined transfer resistance, as defined above in Example III, were obtained by calculating the sum of the water transfer resistance and the oil transfer resistance of each sample. The results for Samples 11 through 17 are quantified on the basis of the Star Grading System as shown below in Table 9.

TABLE 9

| | Transfer Resistance Properties | | |
|---|---|---|---|
| Sample Number: | Water Transfer Resistance | Oil Transfer Resistance | Combined Transfer Resistance |
| 3[1] | 2.8 | 4 | 6.8 |
| 11 | 3 | 4 | 7 |
| 12 | 3 | 4 | 7 |
| 13 | 3 | 4 | 7 |
| 14 | 3 | 3 | 6 |
| 15 | 3 | 3 | 6 |
| 16 | 3 | 2 | 5 |
| 17 | 3 | 1 | 4 |

[1]Sample 3 is represented by the average Star Grading value of 9 transfer resistance tests for Sample 3B Interestingly, the water transfer resistance appears to be independent of silicone polyurethane concentration, yielding a value of about 3 Star Rating units across a greater than 4-fold concentration range. In contrast, the dose-response for oil transfer resistance increased at low concentration, then plateaus above 10% by weight.

Samples 18 through 20 were prepared to investigate the effect of different amounts of silicone polyurethane, in the presence of silicone gum, to the transfer resistance of a lip product. The silicone polyurethane polymer for Samples 18 through 20 is the same as the silicone polyurethane used for Samples 3 through 17. All materials used in the formulations in Table 10 are the same as previously described and all weights represent the weight percent of neat materials.

TABLE 10

| | Sample Number: | | | | | |
|---|---|---|---|---|---|---|
| | 4 | 6 | 18 | 19 | 20 | 10 |
| Components | Weight % | | | | | |
| Silicone Polyurethane MR-20-41 (Siltech Corp.) | — | 12.00 | 8.00 | 6.00 | 4.00 | 6.00 |
| Silicone Gum SE 63 (GE Silicones) | 18.00 | 6.00 | 6.00 | 6.00 | 6.00 | 12.00 |
| Permethyl 98B (Presperse, Inc.) | — | — | — | — | — | — |
| Caprylyl Glycol | 0.50 | 0.50 | 0.50 | 0.50 | 0.50 | 0.50 |
| Tinoguard | 0.05 | 0.05 | 0.05 | 0.05 | 0.05 | 0.05 |
| Bentone Gel | 10.00 | 10.00 | 10.00 | 10.00 | 10.00 | 10.00 |
| Pigment | 10.00 | 10.00 | 10.00 | 10.00 | 10.00 | 10.00 |
| Isododecane | q.s. | q.s. | q.s. | q.s. | q.s. | q.s. |
| Total | 100.00 | 100.00 | 100.00 | 100.00 | 100.00 | 100.00 |

The water and oil transfer resistance properties were obtained using the method described in Example II. The combined transfer resistance, as defined above, was obtained by summing the water transfer resistance and the oil transfer resistance for each sample. The results, quantified on the basis of the Star Grading System, are shown below in Table 11.

TABLE 11

| | Transfer Resistance Properties | | |
|---|---|---|---|
| Sample Number: | Water Transfer Resistance | Oil Transfer Resistance | Combined Transfer Resistance |
| 4 | 4 | 1 | 5 |
| 6 | 5 | 5 | 10 |
| 18 | 4 | 4 | 8 |
| 19 | 4 | 4 | 8 |
| 20 | 4 | 2 | 6 |
| 10 | 5 | 3 | 8 |

FIG. 1 illustrates the water transfer resistance of lip gloss formulations comprising silicone polyurethane in the absence of an elastomer, e.g., lip gloss formulations provided in Table 8 (Samples 3 and 11-17), with the symbol (♦) as a function of the amount of silicone polyurethane (by weight %). The water transfer resistance of lip gloss formulations comprising different concentrations of silicone polyurethane with 6 weight % silicone gum is represented by the symbol (■). As can be seen, the water transfer resistance curve of (■) is above the water transfer resistance curve of (♦) at all data points, further demonstrating that the addition of silicone gum improves the water transfer resistance of a lip gloss formulation comprising a silicone polyurethane copolymer. The water transfer resistance for a lip gloss formulation comprising silicone polyurethane and 12% by weight silicone gum (Sample 10), as shown with the symbol (▲) in FIG. 1, also lies above the water transfer resistance curve of (♦), further illustrating this broad synergy. The water transfer resistance for Sample 4 comprising silicone gum in the absence of silicone polyurethane polymer is also illustrated in FIG. 1 by a dotted line. This dotted line is provided for comparison but does not represent the water transfer resistance of samples including silicone polyurethane.

The dose-response curve of the samples of Table 8, represented by (♦), shows that water transfer resistance of the lip gloss formulations comprising silicone polyurethane in the absence of elastomer is independent of the amount of silicone polyurethane present across silicone polyurethane concentrations from about 4 weight % to about 18 weight %, each concentration giving a Star Grading of 3 except for Sample 3, which is nevertheless very close to 3 (average Star Grading 2.8). As discussed above, the relative instability of the lip gloss formulation at 18% by weight silicone polyurethane, alone, likely gives rise to the minor experimental deviation observed for this sample, but is not considered to be significant.

The results show that lip gloss formulations comprising silicone polyurethane and silicone gum at ratios of 1:2 and 2:1 demonstrate a synergistic improvement in water transfer resistance. Notably, Sample 6 (■), which includes silicone polyurethane and silicone gum in a ratio of 2:1, and Sample 10 (▲), which includes silicone polyurethane and silicone gum in a ratio of 1:2, both show a superior Star Grading of 5 as compared to lip gloss formulations of Table 8 (♦), and the water transfer resistance for a lip gloss formulation comprising 18 weight % silicone gum as represented by the horizontal dotted line at a moderately inferior Star Grading of 4.

Figure 2:
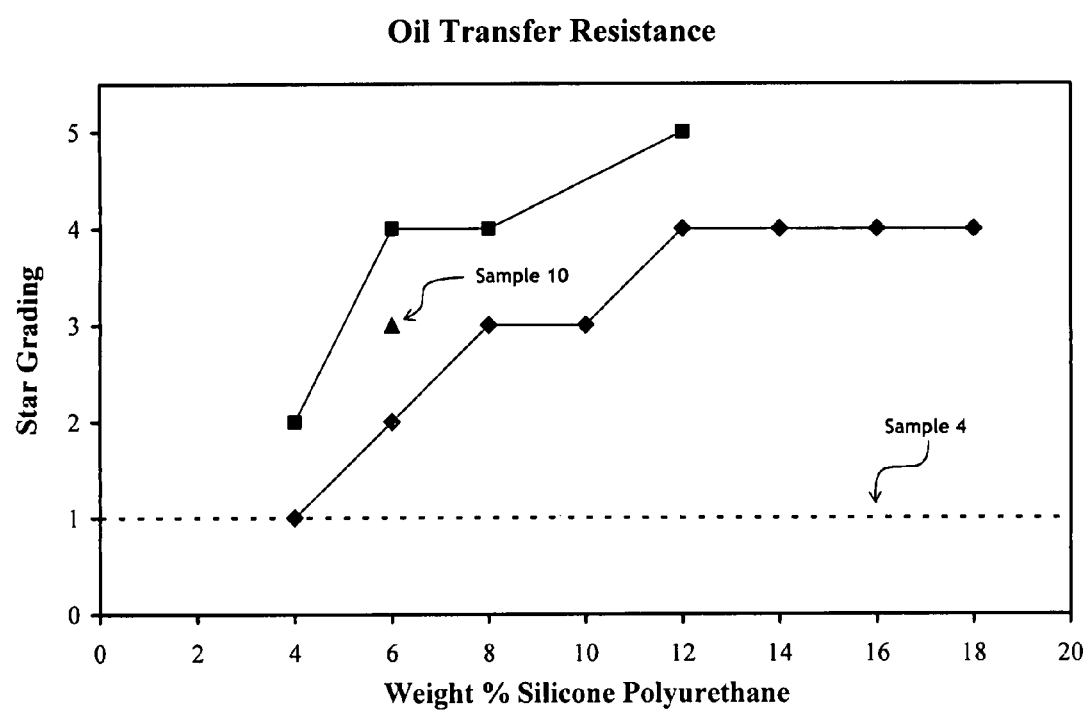
FIG. 2 illustrates the oil transfer resistance of lip gloss formulations comprising silicone polyurethane in the absence of an elastomer (♦) as a function of the amount of silicone polyurethane (by weight %) compared to the oil transfer resistance of lip gloss formulations comprising varying concentrations of silicone polyurethane in combination with 6 weight % silicone gum elastomer (■), and a lip gloss formulation comprising silicone polyurethane in combination with 12% by weight silicone gum (▲).

FIG. 2 illustrates the oil transfer resistance of lip gloss formulations of Table 8 and Table 10 as a function of silicone polyurethane concentration. Lip gloss formulations comprising varying amounts of silicone polyurethane (without elastomer) are represented by the symbol (♦), and formulations comprising varying amounts of silicone polyurethane with 6 weight % silicone gum are represented by the symbol (■).

The water transfer resistance for Sample 10, which comprises silicone polyurethane and 12% silicone gum, is shown with the symbol (▲). The oil transfer resistance for Sample 4 is illustrated with a dotted line as an exemplary lip gloss formulation comprising silicone gum in the absence of silicone polyurethane polymer.

The results suggest that silicone polyurethane polymer and silicone gum in lip gloss formulations act synergistically to impart oil transfer resistance. The oil transfer resistance curve (♦) steadily increases at silicone polyurethane concentrations from 4 weight % to 12 weight % and at silicone polyurethane concentrations above 10 weight %, more specifically at silicone polyurethane concentrations between 12 weight % to 18 weight %, the oil transfer resistance curve plateaus to a Star Grading of 4. As can be seen in FIG. 2, the oil transfer resistance curve of the synergistic combination (■) lies above the oil transfer resistance curve of silicone polyurethane alone (♦) for all data points and is also above the oil transfer resistance for 18 weight % silicone gum (dotted line). Notably, at 12 weight % silicone polyurethane, the synergistic combination (■) has a Star Grading of 5, surpassing the oil transfer resistance observed in lip gloss formulations comprising silicone polyurethane in the absence of an elastomer (♦), which increases at low concentrations of silicone polyurethane but plateaus at a moderate Star Grading of 4. Similarly, Sample 10 (▲) is superior on the basis of oil transfer resistance as compared to: (1) the lip gloss formulations of Table 8 (♦); and (2) Sample 4, as represented by the horizontal dotted line at the minimum possible Star Grading of 1.

Figure 3:
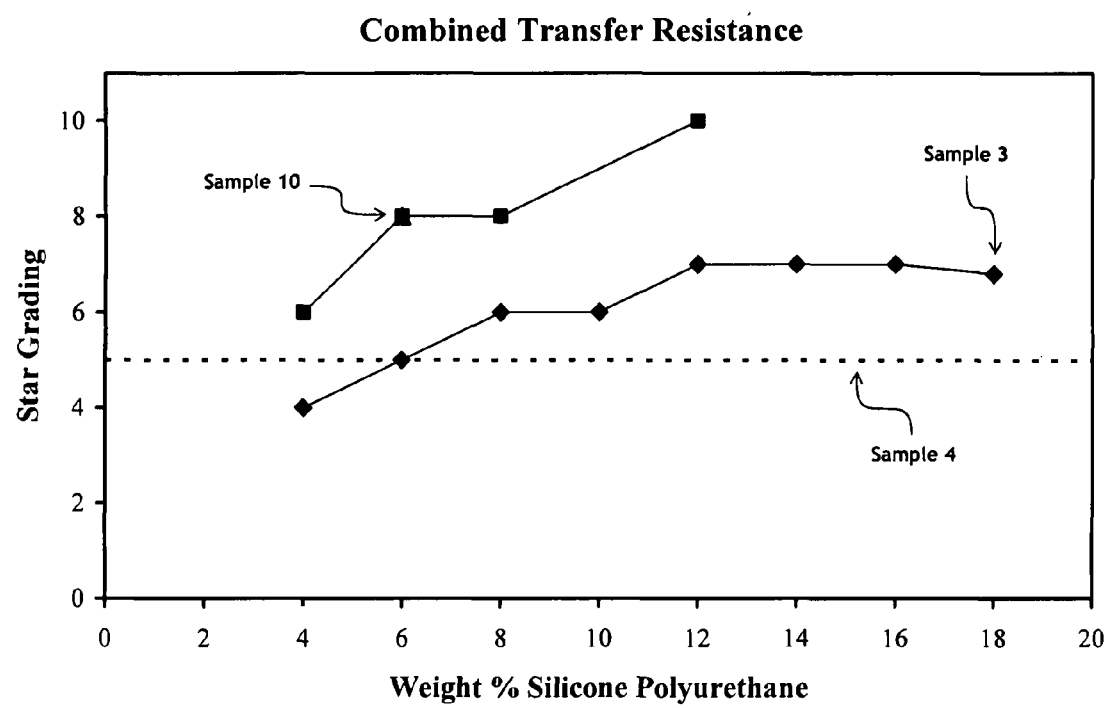
FIG. 3 illustrates the combined oil and water transfer resistance of lip gloss formulations comprising silicone polyurethane in the absence of an elastomer (♦) as a function of the amount of silicone polyurethane (by weight %) compared to the combined oil and water transfer resistance of lip gloss formulations comprising varying concentrations of silicone polyurethane in combination with 6 weight % silicone gum elastomer (■), and a lip gloss formulation comprising silicone polyurethane in combination with 12% by weight silicone gum (▲).

FIG. 3 illustrates the combined transfer resistance of lip gloss formulations of Tables 8 and 10 as a function of silicone polyurethane concentration where the lip gloss formulations comprising silicone polyurethane but no elastomer of Table 8 are represented with the symbol (♦) and lip gloss formulations of Table 10 comprising silicone polyurethane and 6 weight % silicone gum are represented by the symbol (■). Sample 10, which comprises silicone polyurethane and 12 weight % silicone gum is illustrated with the symbol (▲) in FIG. 3. The combined transfer resistance for Sample 4 comprising silicone gum in the absence of silicone polyurethane polymer is illustrated with a dotted line.

The combined transfer resistance curve (♦) steadily increases at silicone polyurethane concentrations from 4 weight % to 12 weight %. At silicone polyurethane concentrations between 12 weight % to 18 weight %, the oil transfer resistance curve plateaus to about a Star Grading of 7. As shown in FIG. 3, at 18 weight % (Sample 3), the combined transfer resistance of (♦) diverges slightly below the Star Grading of 7 whereas other samples above 12 weight % (Samples 11-13) show a Star Grading of 7 although this difference is not considered significant.

The results suggest that silicone polyurethane polymer and silicone gum in lip gloss formulations act synergistically to impart transfer resistance on the basis of the combined parameter of oil and water transfer resistance. The addition of silicone gum to lip gloss formulations comprising silicone polyurethane provides overall superiority based on the combined parameters of water transfer and oil transfer resistance as compared to lip gloss formulations without the synergistic combination of the present invention. As shown in FIG. 3, the combined transfer resistance curve (■) lies above the combined transfer resistance curve (♦) for all data points and is also above the combined transfer resistance for 18 weight % silicone gum (Sample 4) as represented by the dotted line. In particular, at and above 6 weight % silicone polyurethane, the combined transfer resistance curve (■) surpasses the combined transfer resistance observed for lip gloss formulations comprising silicone polyurethane in the absence of an elastomer (♦). Similarly, Sample 10 (▲) is superior on the basis of combined oil and water transfer resistance as compared to lip gloss formulations of Table 8 (♦) and Sample 4 (dotted line).

EXAMPLE V

Frequency Sweep Rheology Test

The viscoelastic properties, which quantify the flow and deformation behaviors were examined for (A) silicone polyurethane, (B) silicone gum, (C) polyisobutylene, (D) silicone polyurethane with silicone gum, and (E) silicone polyurethane with polyisobutylene using a frequency sweep rheology test. The frequency sweep rheology test examines the effect of shear frequency or shear rate on the microstructural properties of a material through the response of the material to a range of shear rates. Specifically, the frequency sweep rheology test described below measures the storage modulus (G') and the loss modulus (G") as a function of shear rates.

A Paar Physica USD200 Universal rotational rheometer was used to measure the storage modulus (G') and the loss modulus (G") of each sample. The storage modulus (G') and the loss modulus (G") for each sample was measured at different shear rates varying from 0.1 $sec^{-1}$ to 100 $sec^{-1}$. The measurements were obtained using a cone-and-plate geometry, where each sample is placed onto a fixed plate of the rheometer while a moveable cone is brought into contact with the sample and applies a shear to the sample. Each samples is maintained at a temperature of 33° C. as the storage modulus (G') and the loss modulus (G") are measured at different shear rates.

A frequency sweep test measuring the storage modulus (G') was conducted for compositions of silicone polyurethane MR-20-41 (Siltech Corporation) (40 weight % in IDD) (A), silicone gum SE63 (GE Silicones) (50 weight % in IDD) (B), and polyisobutylene Permethyl 98B (Presperse, Inc.) (50 weight % in IDD) (C). The frequency sweep test was also conducted for mixed compositions of silicone polyurethane (22.2 weight %) with silicone gum (22.2 weight %) in IDD (D) and silicone polyurethane (22.2 weight %) with polyisobutylene (22.2 weight %) in IDD (E). The results of the frequency sweep test for the storage modulus (G') and the loss tangent (tan δ) of these compositions are illustrated as a function of the frequency, or shear rate, in FIGS. 4 and 5, respectively. At high shear rates, the loss tangent (tan δ) appears to plateau at about $10^6$, but this is merely a limitation of the rheometer used and represents the maximum loss tangent measurable at these values. In actuality, the loss tangent will have the shape of a tangent function, with a vertical asymptote.

Figure 4:
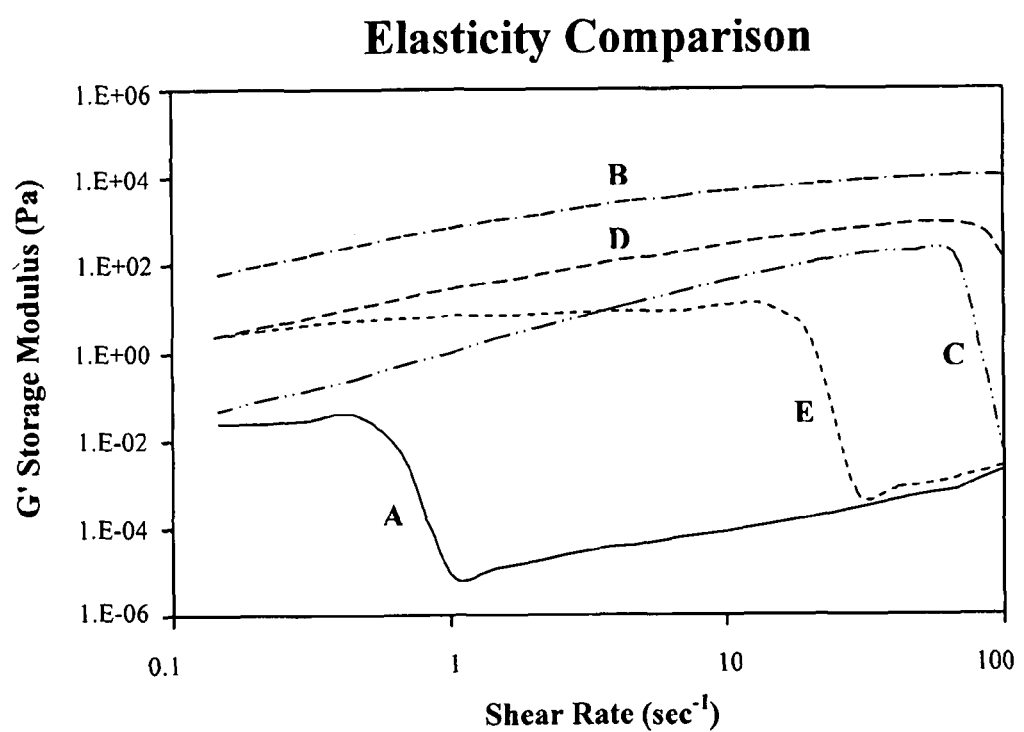
FIG. 4 shows the storage modulus (G') as a function of shear rate for: a silicone polyurethane polymer (A); a silicone gum elastomer (B); a polyisobutylene elastomer (C); a synergistic combination of silicone polyurethane polymer and silicone gum elastomer (D); and a synergistic combination of silicone polyurethane polymer and polyisobutylene elastomer (E).
Figure 5:
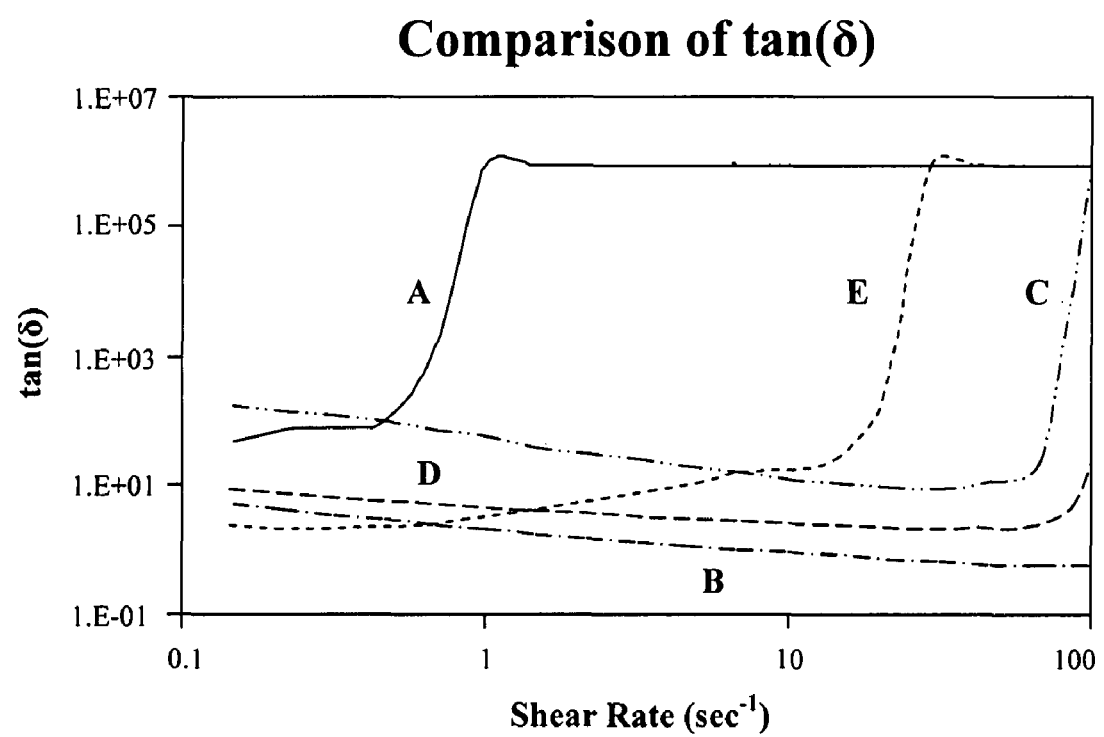
FIG. 5 shows the loss tangent, (tan δ) as a function of shear rate for: a silicone polyurethane polymer (A); a silicone gum elastomer (B); a polyisobutylene elastomer (C); a synergistic combination of silicone polyurethane polymer and silicone gum elastomer (D); and a synergistic combination of silicone polyurethane and polyisobutylene elastomer (E).

Polydimethylsiloxane polyurethane does not have balanced viscoelastic properties because, while it is highly viscous, it is poorly elastic. FIG. 4 shows the G' storage modulus of a representative polydimethylsiloxane polyurethane, silicone polyurethane MR-20-41 (Siltech Corporation) (40 weight % in IDD) (A), as a function of shear rate in inverse seconds. As can be seen in FIG. 4, the G' storage modulus for silicone polyurethane (A) breaks down sharply at low shear (below 1 $sec^{-1}$) which indicates that even at low shear rates the polymer has little elasticity but high viscosity. The sharp drop in G' storage modulus for this material is due to the dissipation of the stored energy to the system in the form of heat owing to the viscous nature of the polymer. In other words, at low shear rates, the loss modulus G" becomes very large.

The elastomers are by definition highly elastic and thus, are characterized by a G' storage modulus that is relatively steady or increasing over a wide range of shear rates, for example from shear rates of 0.1 to 50 sec$^{-1}$ or from 0.1 to 100 sec$^{-1}$ or even higher. The elastomers do not exhibit a break down in G' storage modulus at low shear rates as seen with the polyorganosiloxane polyurethane polymer (A). Rather, elastomers maintain relatively steady values for the G' storage modulus over a wide range of shear rates. The G' storage modulus for an exemplary silicone gum elastomer, SE63 (GE Silicones) (50 weight % in IDD) (B), remains highly elastic over broad range of shear rages, including and beyond 100 sec$^{-1}$. Another example of an elastomer is a polyisobutylene Permethyl 98B (Presperse, Inc.) (50 weight % in IDD) (C), which remains highly elastic over a broad range of shear rates and the G' storage modulus break down only at shear rates approaching 100 sec$^{-1}$.

The inclusion of elastomers in the cosmetic composition imparts an elastic component to balance the viscosity of the polyorganosiloxane polyurethane polymer, providing a cosmetic composition having ideal viscoelastic properties. As seen in FIG. 4, the exemplary mixed compositions (D and E) comprising silicone polyurethane and elastomer demonstrate relatively linear storage modulus (G') at low shear rates (from about 0.1 to about 10 sec$^{-1}$), corresponding to the range of shear rates typically encountered during wear, and begin to break down at shear rates between about 10 to about 100 sec$^{-1}$, which correspond to a range of shear forces typically encountered during application of the cosmetic composition to the skin. Accordingly, the mixed compositions begin to transition from having balanced viscoelastic properties to having predominantly viscous properties at these higher shear rates and thus exhibit beneficial viscoelastic properties at shear forces typically encountered during wear but allow for excellent pay-off during application of cosmetic. As demonstrated in FIG. 5, the exemplary mixed compositions (D and E) also demonstrate desirable viscoelastic properties, as quantified by having a loss tangent value between about 1 to about 10, for low shear rates and a sharp, discontinuous rise occurring at a shear rates between about 10 to about 100 sec$^{-1}$.

EXAMPLE VI

Cosmetically optimized lip gloss formulations, Samples 21 through 25, were prepared according to the formulations shown in Table 12, which provides the converted weights representing the weight % of neat silicone polyurethane copolymer, neat silicone gum, and/or neat polyisobutylene in each sample formulation (i.e., in the absence of IDD). Samples 21 and 25 comprises elastomer but not silicone polyurethane copolymer. Samples 23 and 24 comprise 18.00% by weight of silicone polyurethane polymer and either 9.33% by weight of silicone gum or 14.00% by weight of polyisobutylene, respectively. Sample 22 comprises a combination of silicone polyurethane copolymer, silicone gum and polyisobutylene.

TABLE 12

| | Sample Number: | | | | |
|---|---|---|---|---|---|
| | 21 | 22 | 23 | 24 | 25 |
| Components | | | Weight % | | |
| Silicone Polyurethane MR-20-41 (Siltech Corp.) | — | 17.60 | 18.00 | 18.00 | — |

TABLE 12-continued

| | Sample Number: | | | | |
|---|---|---|---|---|---|
| | 21 | 22 | 23 | 24 | 25 |
| Components | | | Weight % | | |
| Silicone Gum SE 63 (GE Silicones) | 20.00 | 5.00 | 9.33 | — | — |
| Permethyl 98B (Presperse, Inc.) | — | 7.50 | — | 14.00 | 25.00 |
| Caprylyl Glycol | — | 0.50 | 0.50 | 0.50 | 0.50 |
| Tinoguard | — | 0.05 | 0.05 | 0.05 | 0.05 |
| Bentone Gel | 6.00 | 5.00 | 5.00 | 5.00 | 10.00 |
| Dow Corning ® 9701 cosmetic powder | — | 1.00 | 1.00 | 1.00 | — |
| Jetmilled Pigment | 10.00 | 11.00 | 11.00 | 11.00 | 12.00 |
| Isododecane | q.s. | q.s. | q.s. | q.s. | q.s. |
| Total | 100.00 | 100.00 | 100.00 | 100.00 | 100.00 |

The water and oil transfer resistance properties were obtained using the method described in Example II. The results for Samples 21 through 25 are also quantified on the basis or the star Grading System as shown below in Table 13.

TABLE 13

| | Transfer Resistance Properties | |
|---|---|---|
| Sample Number: | Water Transfer Resistance | Oil Transfer Resistance |
| 21 | 2 | 5 |
| 22 | 5 | 3 |
| 23 | 5 | 4 |
| 24 | 4 | 3 |
| 25 | 2 | 5 |

A frequency sweep test measuring the storage modulus (G') and loss modulus (G") was conducted for Sample 1 from Example 1 and Samples 11 through 15. The results of the frequency sweep test for the storage modulus (G') and the loss tangent (tan δ) of these compositions are illustrated as a function of the shear rate in FIGS. 6 and 7, respectively.

Figure 6:
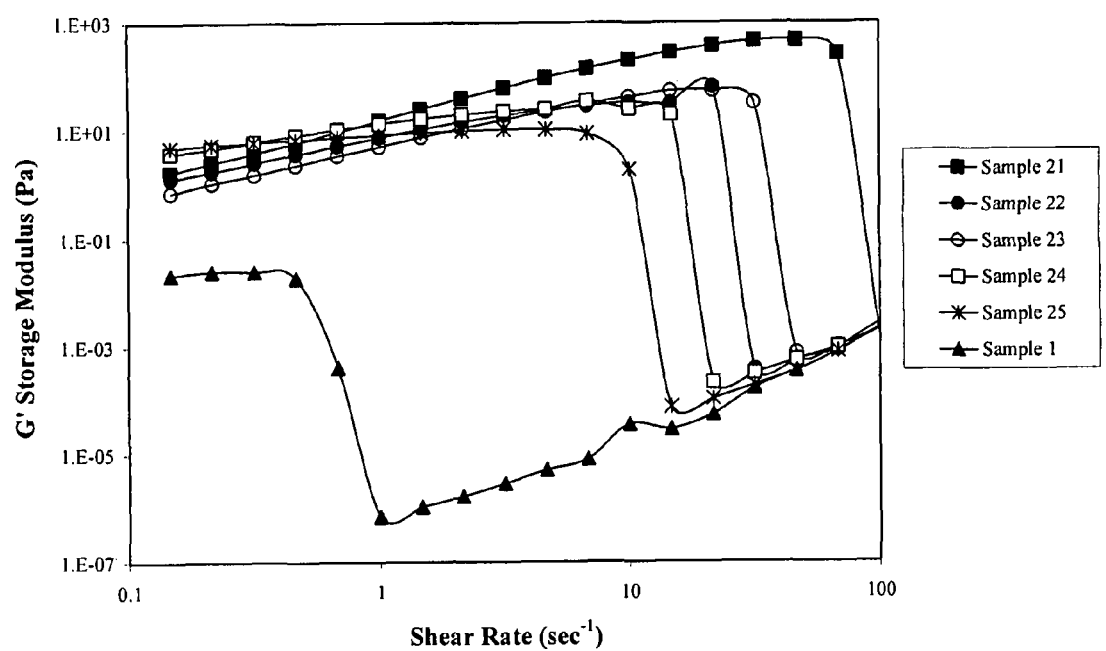
FIG. 6 shows the storage modulus (G') as a function of shear rate for lip gloss formulations of Sample 1 of Example II and Samples 21-25 of Example VI.
Figure 7:
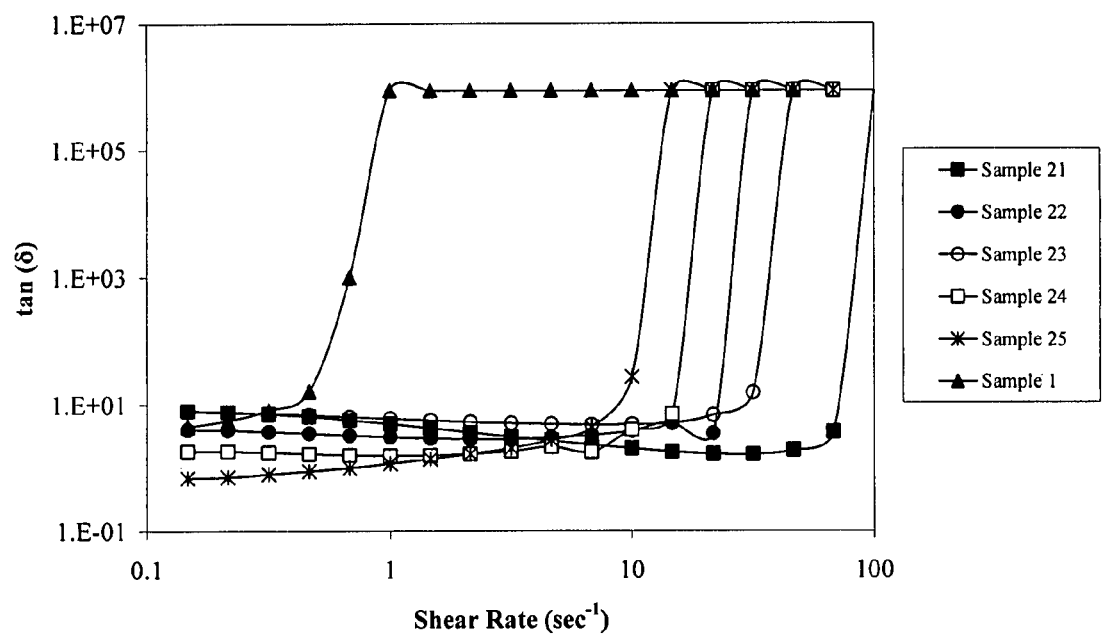
FIG. 7 shows the loss tangent (tan δ) as a function of shear rate in inverse seconds for lip gloss formulations of Sample 1 of Example II and Samples 21-25 of Example VI.

The cosmetically optimized lip gloss formulations begin to transition from having elastic properties to having viscous properties above shear rates typically encountered during wear, about 0.1 to about 10 sec$^{-1}$, for all samples except Sample 1, indicating that the formulations have desirable viscoelastic properties and consequently greater substantivity to the skin. As shown in FIG. 6, Sample 22 demonstrate relatively linear storage modulus (G') at low shear rates (from about 0.1 to about 10 sec$^{-1}$), corresponding to the range of shear rates typically encountered during wear, but begins to break down at a shear rate about 22 sec$^{-1}$, which is within a range of shear forces typically required for application of the cosmetic composition to the skin. Sample 23 and 24 also show relatively linear storage modulus at low shear rates, and begin to break down at shear rates about 32 sec$^{-1}$ and about 15 sec$^{-1}$, respectively. Thus, the lip gloss formulations having the synergistic combination of the invention (Samples 22-24) are expected to possess good substantivity to the skin during wear but also will be easy to apply. As demonstrated in FIG. 7, the cosmetically optimized lip gloss formulations having the synergistic combination (Samples 22, 23 and 24) also demonstrate desirable viscoelastic properties, as quantified by having a loss tangent value between about 1 to about 10, for low shear rates of about 0.1 sec$^{-1}$ to about 5, 6, 7, 8, 9, 10 sec$^{-1}$ and begin to exhibit a sharp, discontinuous rise at shear rates about 22 sec$^{-1}$, about 32 sec$^{-1}$, and about 15 sec$^{-1}$, respectively. These beneficial viscoelastic properties are believed to contribute to the superior water transfer resistance for Samples 22, 23 and 24 which give a Star Grading of 5, 5, and 4, respectively, in contrast to the inferior Star Grading of 2 for Samples 21 and 25, which do not include the synergistic combination of the present invention.

Film Flexibility Test

The flexibility of Samples 22-25 were examined using a modification of the flexibility testing protocol described in U.S. Pat. No. 6,074,654, the contents of which are hereby incorporated by reference. The flexibility of a cosmetic film is important to both the durability (long-wear) and comfort properties of a cosmetic film.

Flexibility is measured by the latex stretch test. This test predicts the ability of the color film to resist flaking or peeling types of failure after application by movement of the skin during normal activities. The flexibility latex stretch test is based on the weight-loss measurement before and after the latex stretch.

Equipment:
(1) Ansell Industrial technicians unlined gloves (12" length, 17 mil) USDA Accepted #390, Size 9;
(2) Slanted Eyeshadow Brushes from Avon Products, Inc.
(3) Analytical balance (4 decimal places); and
(4) Ruler.

Procedure:
(1) Cut a 1 inch wide band from the wrist area of the glove, avoiding the ribbing and thumb.
(2) Mark off a 1×1 inch block in the center of smooth side of the band, avoiding the embossed number.
(3) Weigh and record the weight of the latex band; hereinafter referred to as A.
(4) Determine the initial weight of the cosmetic to be applied to the band in order to produce a dried film weighing 20 mg. This is determined by dividing 20 mg by the weight percent of non-volatile material present in the cosmetic. For example, 40 mg of a cosmetic with 50% non-volatile content must be applied to the band in order to yield a 20 mg dried film.
(5) Using a clean eyeshadow brush, evenly apply the amount of cosmetic determined in step (4) over the 1×1 inch area of the band as marked in step (2).
(6) Immediately weigh and record the combined weight of the latex band and applied cosmetic. The weight of wet film with the latex band is referred to as B.
(7) Allow the sample on the latex band from step (6) to sit at ambient room conditions for one hour.
(8) Weigh and record the combined weight of the latex band A and the applied cosmetic film; hereinafter referred to as C. Subtract A from C to determine the dried film weight D (D=C−A). This weight should be 20±2 mg.
(9) Gently stretch the latex band so that the marked film length changes from 1.00 inches to 1.75 inches.
(10) Upon observing loosened film pieces on the latex band, remove the film pieces from the latex band by vigorously wiping a clean eyeshadow brush across the surface of the film: 10 times wiping in vertical direction and 10 times wiping in horizontal direction.
(11) Carefully allow the latex band to return to its approximate original shape.
(12) Record the weight of the latex band (with the remaining cosmetic); herein referred to as E.
(13) A "Star Grading System" is used based on percentage weight loss ("PWL") to grade the flexibility of the films as follows:

TABLE 14

Flexibility Star Grading System

| Weight Loss | Scale |
|---|---|
| 100-50% | * |
| 30-50% | ** |
| 15-30% | *** |
| 5-15% | **** |
| 0-5% | ***** |

The percent weight loss of the cosmetic film is calculated using the following equation:

$$\text{Percent Weight Loss(PWL)} = [1-(E-A)/(C-A)] \times 100\%$$

For some very flexible films, the percentage weight loss may be negligible. Therefore, in some case, due to some dust transferred from the brush, the PWL value may become negative (weight gain).

Steps (1) through (12) are repeated three times for each cosmetic formulation tested. The average of the three PWL values is determined; herein referred to as Average Percent Weight Loss ("APWL"). Low APWL values (i.e., 0-5%) correspond to flexible films having a desirable adhesive and cohesive balance of the film. The flexibility test results for Samples 22-25 are quantified on the Star Grading System as shown in Table 15.

TABLE 15

| Sample Number: | Flexibility Star Grading |
|---|---|
| 22 | ***** |
| 23 | ***** |
| 24 | ***** |
| 25 | ***** |

All patents and patent publications referred to herein are hereby incorporated by reference.

Certain modifications and improvements will occur to those skilled in the art upon a reading of the foregoing description. It should be understood that all such modifications and improvements have been deleted herein for the sake of conciseness and readability but are properly within the scope of the following claims.

The invention claimed is:

1. A cosmetic composition comprising a synergistic combination of:
(i) a silicone polyurethane polymer comprising alternating units of A and B, where:
unit A has the structure:

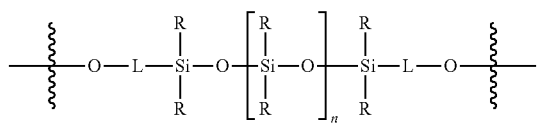

wherein R is selected, independently at each occurrence from optionally substituted, branched, straight chain, or cyclic alkyl, alkenyl, alkynyl, aryl, alkyl-aryl, arylalkyl groups having from 1 to 10 carbon atoms, or R a group -L-O— thereby introducing branching points in unit A; and L is a linker group selected from optionally substituted-branched, straight chain, or cyclic divalent alkyl, alkenyl, alkynyl, aryl, alkyl-aryl, or aryl-alkyl groups having from 1 to 10 carbon atoms, and n is an integer from 0 to 5,000, and unit B has the structure:

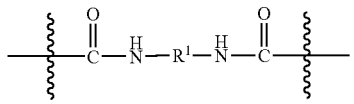

wherein $R^1$ is and optionally substituted, branched, straight chain, or cyclic alkenyl, alkynyl, aryl, alkyl-aryl, or aryl-alkyl groups having from 1 to 20 carbon atoms;

and wherein units A and B form a cyclic polymer of the form

where z is an integer from 2 to 2,000; and an elastomeric component comprising one or more elastomers selected from the group consisting of silicone gums, polyisobutylene, natural rubbers, and block-co-polymer rubbers;

wherein said synergistic combination comprises a weight ratio of silicone polyurethane polymer to elastomeric component from about 50:1 to about 1:50; and where said synergetic combination provides an improvement in one or more characteristic selected from the group consisting of water transfer resistance, oil transfer resistance, durability, and rheology.

2. The cosmetic composition of claim 1 wherein said elastomeric component comprises silicone gum.

3. The cosmetic composition of claim 1 wherein said elastomeric component comprises polyisobutylene.

4. The cosmetic composition of claim 1 wherein said synergistic combination comprises a weight ratio of silicone polyurethane polymer to elastomeric component from about 25:1 to about 1:25.

5. The cosmetic composition of claim 1 wherein said synergistic combination comprises a weight ratio of silicone polyurethane polymer to polyorganosiloxane gum from about 10:1 to about 1:10.

6. The cosmetic composition of claim 1 wherein said synergistic combination comprises a weight ratio of silicone polyurethane polymer to polyorganosiloxane gum from about 5:1 to about 1:5.

7. The cosmetic composition of claim 1 wherein said synergistic combination comprises a weight ratio of silicone polyurethane polymer to polyorganosiloxane gum from about 3:1 to about 1:3.

8. The cosmetic composition of claim 1 wherein said synergistic combination comprises a weight ratio of silicone polyurethane polymer to polyorganosiloxane gum from about 2:1 to about 1:2.

9. The composition of claim 1 wherein said improvement is an improvement selected from the group consisting of water transfer resistance and oil transfer resistance.

10. The composition of claim 9 wherein said improvement is an improvement in water transfer resistance.

11. The composition of claim 1 wherein the composition is one of a lip gloss, a mascara, or a hair care product.

12. A method for imparting a transfer resistant film to a biological surface comprising:

applying to said surface a composition comprising a synergistic combination of (i) a silicone polyurethane polymer comprising alternating units of A and B, where unit A has the structure:

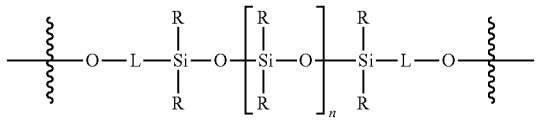

wherein R is selected, independently at each occurrence from optionally substituted, branched, straight chain, or cyclic alkyl, alkenyl, alkynyl, aryl, alkyl-aryl, aryl-alkyl groups having from 1 to 10 carbon atoms, or R a group -L-O— thereby introducing branching points in unit A; where L is a linker group selected from optionally substituted branched, straight chain, or cyclic divalent alkyl, alkenyl, alkynyl, aryl, alkyl-aryl, or aryl-alkyl groups having from 1 to 10 carbon atoms, and n is an integer from 0 to 5,000, and unit B has the structure:

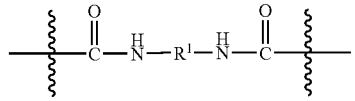

wherein $R^1$ is and optionally substituted, branched, straight chain, or cyclic alkyl, alkenyl, alkynyl, aryl, alkyl-aryl, or aryl-alkyl groups having from 1 to 20 carbon atoms;

and wherein units A and B form a cyclic polymer of the form

where z is an integer from 2 to 2,000; and (ii) at least one elastomer selected from the group consisting of silicone gums, polyisobutylene, natural rubbers, and block-copolymer rubbers, wherein said composition provides improved oil and/or water transfer resistance as compared to an otherwise identical composition in the absence of either said silicone polyurethane polymer or said elastomer.

13. The method of claim 12, wherein said improved transfer resistance comprises improved water transfer resistance.

14. The method of claim 12, wherein said improved transfer resistance comprises improved oil transfer resistance.

15. The method of claim 12, wherein said at least one elastomer comprises silicone gum.

16. The method of claim 12, wherein said at least one elastomer comprises polyisobutylene.

17. The method of claim 12, wherein said synergistic combination comprises a weight ratio of silicone polyurethane polymer to elastomeric component from about 25:11 to about 1:25.

18. The method of claim 12, wherein said synergistic combination comprises a weight ratio of silicone polyurethane polymer to elastomeric component from about 10:1 to about 1:10.

19. The method of claim 12, wherein said synergistic combination comprises a weight ratio of silicone polyurethane polymer to elastomeric component from about 5:1 to about 1:5.

20. The method of claim 12, wherein said synergistic combination comprises a weight ratio of silicone polyurethane polymer to elastomeric component from about 3:1 to about 1:3.

21. The method of claim 12, wherein said synergistic combination comprises a weight ratio of silicone polyurethane polymer to polyorganosiloxane gum from about 2:1 to about 1:2.

22. The method of claim 12, further comprising applying an optionally clear top coat over said transfer resistant film.

* * * * *